US006793658B2

(12) United States Patent
LeHuec et al.

(10) Patent No.: US 6,793,658 B2
(45) Date of Patent: Sep. 21, 2004

(54) ANTERIOR PLATING SYSTEM AND METHOD

(75) Inventors: Jean-Charles LeHuec, Pessac (FR); Mingyan Liu, Bourg la Reine (FR); Loic Josse, Palaja (FR)

(73) Assignee: Society de Fabrication de Material Orthopedique, S.A., Roissy (FR)

( * ) Notice: Subject to any disclaimer, the term of this patent is extended or adjusted under 35 U.S.C. 154(b) by 0 days.

(21) Appl. No.: 09/993,860

(22) Filed: Nov. 6, 2001

(65) Prior Publication Data

US 2002/0147450 A1 Oct. 10, 2002

(30) Foreign Application Priority Data

Apr. 6, 2001 (FR) ............................................ 01 04728

(51) Int. Cl.⁷ .............................................. A61B 17/58
(52) U.S. Cl. .......................................... 606/61; 606/69
(58) Field of Search .............................. 606/61, 69, 70, 606/71

(56) References Cited

U.S. PATENT DOCUMENTS

| | | |
|---|---|---|
| 3,659,595 A | 5/1972 | Haboush |
| 3,695,259 A | 10/1972 | Yost |
| 3,741,205 A | 6/1973 | Markolf et al. |
| 4,289,123 A | 9/1981 | Dunn |
| 4,488,543 A | 12/1984 | Tornier |
| 4,493,317 A | 1/1985 | Klaue |
| 4,503,848 A | 3/1985 | Caspar et al. |
| 4,794,918 A | 1/1989 | Wolter |
| 4,938,769 A | 7/1990 | Shaw |
| 4,944,757 A | 7/1990 | Martinez et al. |
| 4,957,497 A | 9/1990 | Hoogland et al. |
| 4,963,152 A | 10/1990 | Hofmann et al. |
| 5,061,271 A | 10/1991 | Van Zile |
| 5,127,914 A | 7/1992 | Calderale et al. |
| 5,147,361 A | 9/1992 | Ojima et al. |
| 5,180,381 A | 1/1993 | Aust et al. |
| 5,324,290 A | 6/1994 | Zdeblick et al. |
| 5,364,399 A | 11/1994 | Lowery et al. |
| 5,397,363 A | 3/1995 | Gelbard |

(List continued on next page.)

FOREIGN PATENT DOCUMENTS

| | | |
|---|---|---|
| EP | 0 455 255 A1 | 11/1991 |
| EP | 0 599 766 A1 | 6/1994 |
| EP | 0 867 149 A1 | 9/1998 |
| FR | 2 726 755 A1 | 5/1996 |
| FR | 2 740 321 A1 | 4/1997 |
| FR | 2 778 088 A1 | 11/1999 |
| FR | 2 784 571 A1 | 4/2000 |
| WO | WO 95/25474 | 9/1995 |
| WO | WO 97/37620 | 10/1997 |
| WO | WO 99/04718 | 2/1999 |
| WO | WO 99/21502 | 5/1999 |
| WO | WO 99/56653 | 11/1999 |
| WO | WO 00/24325 | 5/2000 |
| WO | WO 00/78238 | 12/2000 |

OTHER PUBLICATIONS

U.S. patent application Ser. No. 09/696,130, Kozak et al., filed Oct. 20, 2000.

*Primary Examiner*—Cary E. O'Connor
*Assistant Examiner*—Candice C. Melson
(74) *Attorney, Agent, or Firm*—Woodard, Emhardt, Moriarty, McNett & Henry LLP

(57) ABSTRACT

Systems and methods for stabilizing the spine are provided. For stabilizing the L5-S1 junction, the system includes a plate that has a generally triangular shape with an upper node and a pair of lower nodes. The upper node has a hole through the plate to receive a screw for passage into the L5 vertebra. The lower nodes each include a hole through the plate to receive screws for passage into the S1 vertebra. The system further includes a plate having a retaining element for preventing backout of screws inserted through the plate. Instruments and methods for attaching the plate to the spinal column are also provided.

46 Claims, 25 Drawing Sheets

U.S. PATENT DOCUMENTS

| | | |
|---|---|---|
| 5,423,826 A | 6/1995 | Coates et al. |
| 5,534,027 A | 7/1996 | Hodorek |
| 5,549,612 A | 8/1996 | Yapp et al. |
| 5,569,250 A | 10/1996 | Sarver et al. |
| 5,578,034 A | 11/1996 | Estes |
| 5,603,713 A | 2/1997 | Aust et al. |
| 5,616,144 A | 4/1997 | Yapp et al. |
| 5,676,666 A | 10/1997 | Oxland et al. |
| 5,785,713 A | 7/1998 | Jobe |
| 5,800,433 A | 9/1998 | Benzel et al. |
| 5,904,683 A | 5/1999 | Pohndorf et al. |
| 5,951,558 A | 9/1999 | Fiz |
| 6,017,345 A | 1/2000 | Richelsoph |
| 6,022,350 A | 2/2000 | Ganem |
| 6,030,389 A | 2/2000 | Wagner et al. |
| 6,045,552 A | 4/2000 | Zucherman et al. |
| 6,139,550 A | 10/2000 | Michelson |
| 6,152,927 A | 11/2000 | Farris et al. |
| 6,156,037 A | 12/2000 | LeHuec et al. |
| 6,193,721 B1 | 2/2001 | Michelson |
| 6,224,602 B1 | 5/2001 | Hayes |
| 6,228,085 B1 | 5/2001 | Theken et al. |
| 6,235,034 B1 | 5/2001 | Bray |
| 6,258,089 B1 | 7/2001 | Campbell et al. |
| 6,261,291 B1 | 7/2001 | Talaber et al. |
| 6,290,703 B1 | 9/2001 | Ganem |
| 6,306,139 B1 | 10/2001 | Fuentes |
| 6,331,179 B1 | 12/2001 | Freid et al. |
| 6,565,571 B1 | 5/2003 | Jackowski et al. |
| 6,652,525 B1 * | 11/2003 | Assaker et al. ............ 606/61 |
| 2002/0022843 A1 | 2/2002 | Michelson |

\* cited by examiner

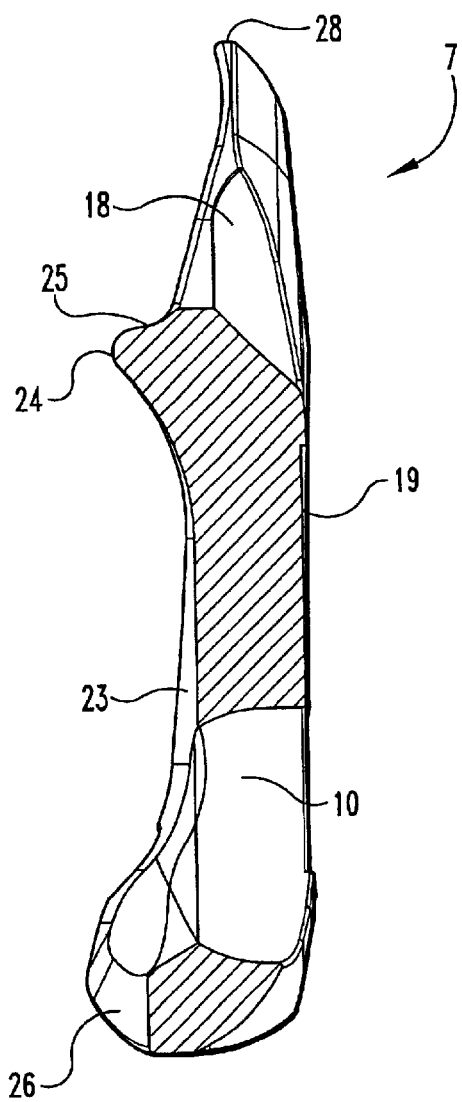 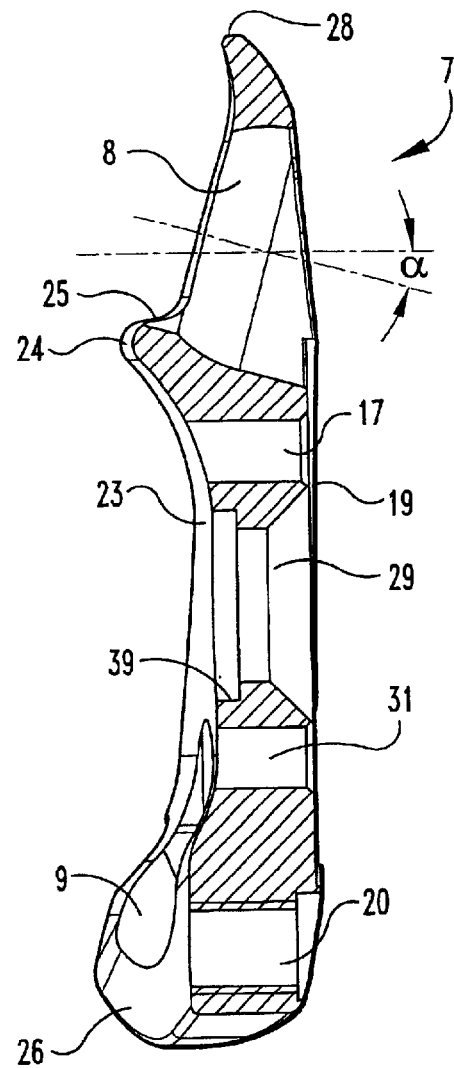
Fig. 3c  Fig. 3b
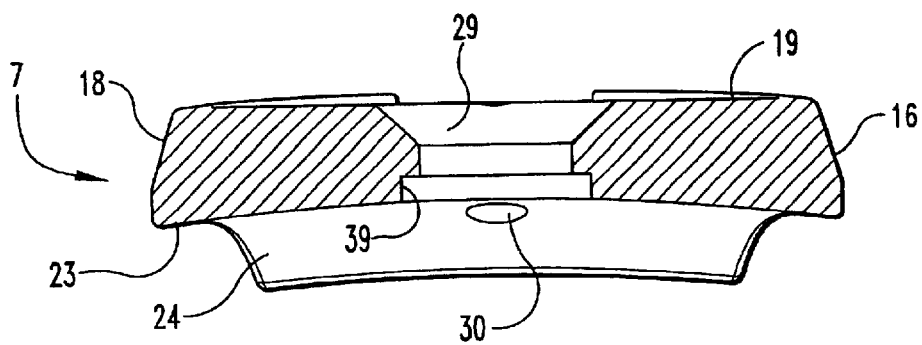
Fig. 3d

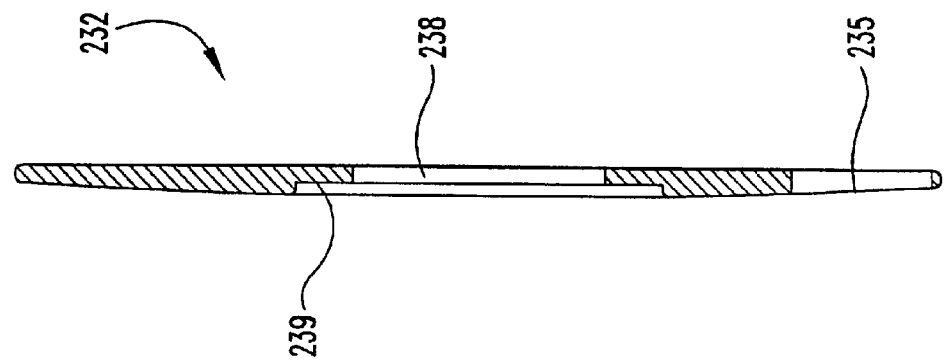
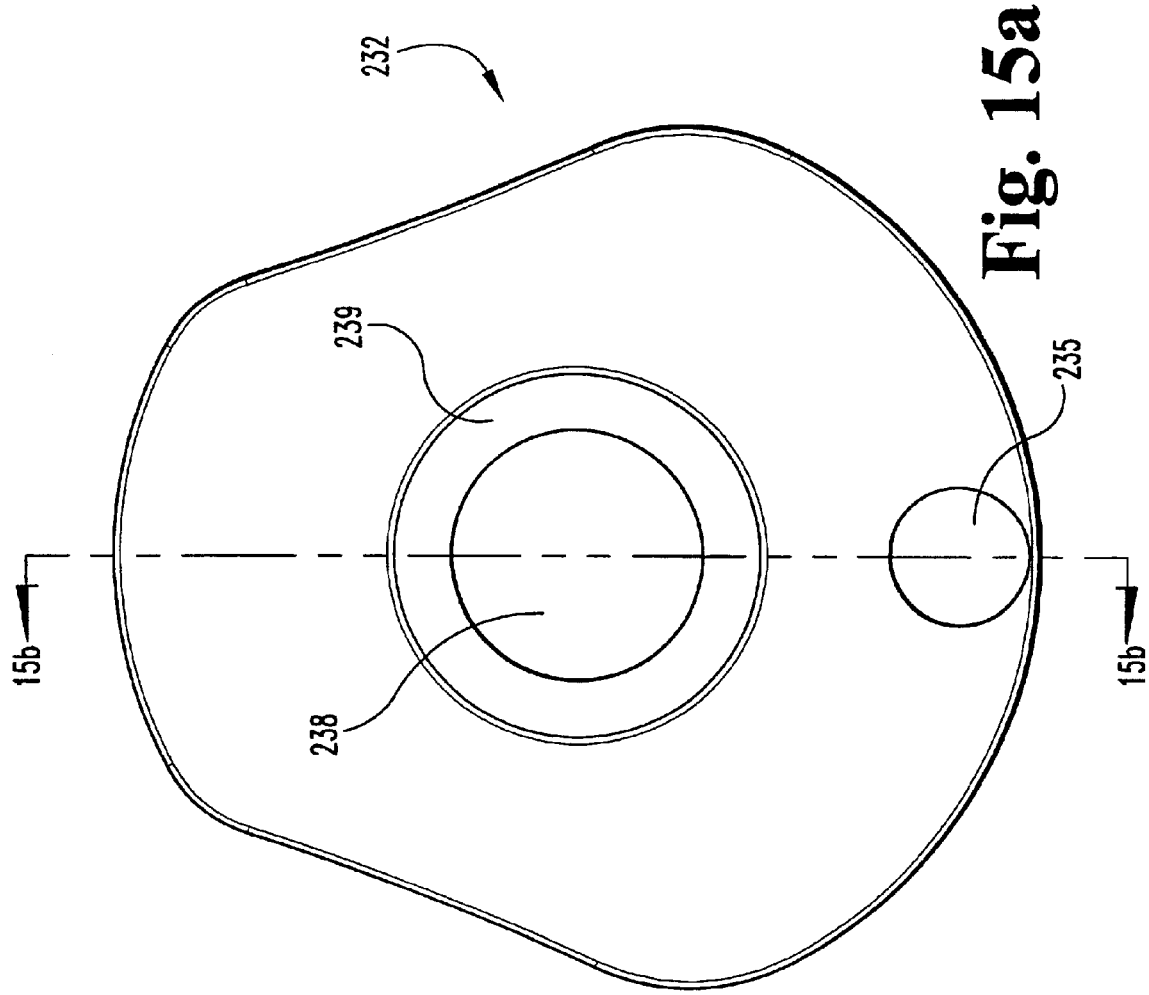

ANTERIOR PLATING SYSTEM AND METHOD

CROSS-REFERENCE TO RELATED APPLICATIONS

The present application hereby claim foreign priority benefits under Title 35, United States Code, §119 to French Patent Application No. 01 04728, filed Apr. 6, 2001.

FIELD OF THE INVENTION

The present invention related generally to instruments and methods for spinal stabilization, and more particularly to spinal plating systems and methods.

BACKGROUND OF THE INVENTION

Various types of plating devices and systems have been used to stabilize portions of the spine. For cases in which interbody fusion is desired in the lumbro-sacral region, stabilization using posterior plating has been preferred by many surgeons for good fixation and to avoid damage to the vascular and nervous system components adjacent the anterior surfaces of the L5 vertebra. A posterior plating system for stabilization of the L5-S1 junction is disclosed in U.S. Pat. No. 5,127,912 issued Jul. 7, 1992 to Ray and Ashman.

While posterior fixation systems are often used in fusions, the anterior surgical approach for insertion of fusion devices is preferred from several perspectives. Less blood loss and reduced post-operative pain can be achieved, and there is risk of traumatizing nerves. Additionally, the posterior approach impairs muscles, which are vascularized, and ligaments, which are cut. Effective anterior plating could generally avoid the risks associated with posterior surgery, particularly if an anterior approach is used which is also as minimally invasive as possible, since it is then only necessary to move aside soft tissues which do not affect the stability of the spinal column.

There is however one zone of the spine where an anterior approach entails a particular risk: the zone corresponding to lumbar vertebrae L4-L5 and the first sacral vertebra S1. In this region, the aorta and the vena cava divide to form the right and left iliac veins and arteries. There is therefore a risk of damaging an important blood vessel during implantation of a conventional fixation system. There is also a risk that important blood vessels could be damaged by screw backout, or simply by protrusion of the plate against the blood vessel. Moreover, between the profiles of vertebrae L5 and S1 there is an angle called the "promontory angle" which is very variable from one individual to another. There can also be sliding between L5 and S1 (spondylolisthesis). These conditions further increase the difficulty and risk factors associated with attachment of a stabilization device anteriorly to the L5-S1 region.

There remains a need for anterior plating systems and methods to provide stability for fusion between vertebrae that is adapted to address the challenges presented above.

SUMMARY OF THE INVENTION

Described briefly according to the illustrated embodiments of the invention, a stabilizer for the lumbar/sacral junction is provided. The stabilizer includes a plate having a generally triangular shape with an upper node and a pair of lower nodes. The upper node has an upper hole to receive a screw for passage into an upper vertebra, such as L5. The lower nodes each include a hole to receive a screw for passage into a lower vertebra, such as S1.

There is also provided a plate for a device for stabilization of vertebrae L5 and S1 that has a generally triangular shape, and includes near its upper vertex, a hole through which a screw is passed for fixing the plate to L5, and two holes situated near its lower vertices through which screws are passed for fixing the plate to S1.

The present invention also provides an anterior spinal plate system that has a plate with a generally triangular shape and includes on its posterior face a protrusion which extends along at least part of the width of the plate that bears against the lower anterior lip of the lower endplate of L5.

The present invention additionally provides an anterior spinal plate system that has a plate with a triangular shape and includes, on its posterior face near its lower vertices, protrusions which are intended to come to bear against the lower margin of the salient part of S1. The plate can further include on the edge of its posterior face, in the region of its upper vertex, a ridge-shaped protrusion or at least one anchoring point or spike to contact or anchor in L5.

The present invention further provides an anterior spinal plate system that has a plate with an upper face, a lower face, and at least one hole therethrough extending between the upper and lower faces. A retaining element extends from the upper face of the plate adjacent the at least one hole. The retaining element has a first form wherein a screw is insertable into the at least one hole and is formable to a second form wherein at least a portion of the retaining element extends over the at least one hole, blocking the screw in the hole.

The present invention further provides an anterior spinal plate system that includes a plate having a triangular shape and an upper face, a lower face, and holes therethrough extending between the upper and lower faces at each vertex. A retaining element is provided to prevent screw backout. In one form, the retaining element can be clipped, screwed or otherwise secured to the anterior face of the plate and is capable of at least partially covering the holes passed through by the screws. The retaining element can be of substantially circular shape, substantially triangular shape, or spoke shaped.

The invention also provides a system for osteosynthesis of the spine for joining vertebrae L5 and S1. The system includes a triangular plate having an upper vertex oriented over L5 and two lower vertices oriented over S1. Each vertex has a hole through which a screw may be passed. The system further includes an interbody device inserted into the disc space separating L5 and S1.

The present invention further contemplates instruments for use during surgical procedures that are used to secure an anterior supplemental fixation plate to the spine. One such instrument includes a plate holder that includes a holding portion mounted on a shaft. The holding portion matches the shape of the lower edge of the plate and is provided with means for establishing and maintaining a defined relative position between the holding portion and the plate. The instrument further includes a support member having guiding portions for directing screws into the plate holes.

The present invention further includes methods for stabilizing a spinal segment. One method includes installing a generally triangular-shaped plate having an upper node along the anterior face of L5 and a pair of lower nodes along the anterior face of S1; installing a first screw from the front of the plate through a single hole in the upper node of the plate into L5; and installing screws from the front of the plate through a hole in each of the lower nodes of the plate and into S1. Variations to the above method and other methods are also contemplated.

The above is intended merely as a summary of various inventive aspects presented in the present application, and is in no way intended to be an exhaustive or all-inclusive recitation of such aspects. Additional aspects, forms, features, embodiments and principles of the present invention will be further described below.

BRIEF DESCRIPTION OF THE DRAWINGS

FIGS. 3a–3d show, respectively, a plan view, a cross section along 3b-3b of FIG. 3a, a cross section along 3c–3c of FIG. 3a, and a cross section along 3d–3d of FIG. 3a, of an example of a plate according to the present invention.

FIG. 14b is a perspective view looking at the posterior side of the plate and retaining element of FIG. 14a.

FIGS. 15a and 15b show, respectively, a plan view and a cross-section through line 15b–15b of FIG. 15a of the retaining element of FIG. 13.

DESCRIPTION OF THE ILLUSTRATED EMBODIMENTS

Figure 1:
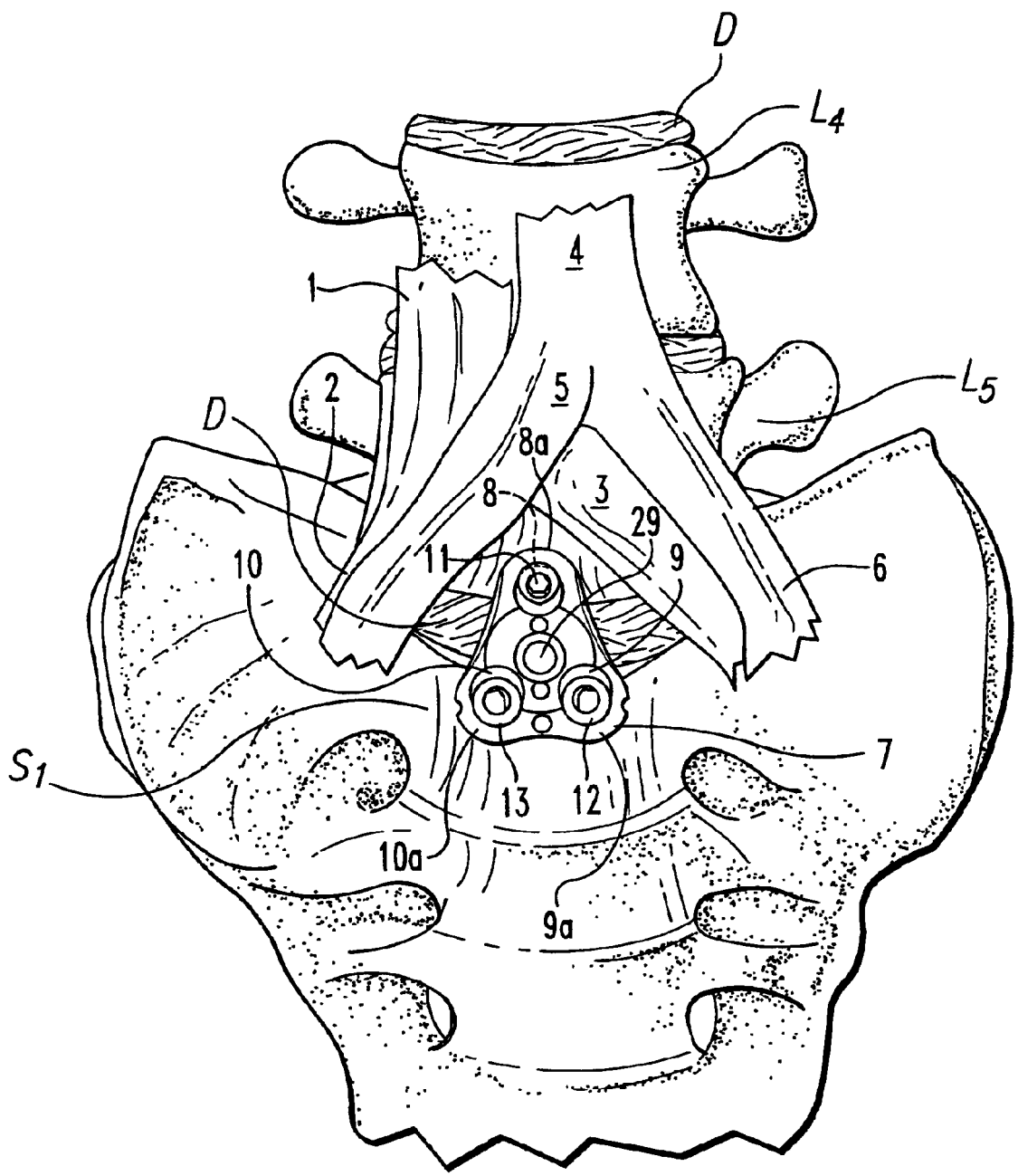
FIG. 1 is a diagrammatic representation of the region of vertebrae L5-S1 where a plating system according to the invention is implanted.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

The present includes a plate in the shape of a triangle. In one application, the plate is inserted in the space available between the left iliac vein and the right iliac artery. The plate is adapted in this way minimize or eliminate interference with the anatomy at the site of implantation. The triangular shape gives the plate a large effective surface area while minimizing the risk of its coming into contact with the blood vessels during its fitting and afterwards. The plate is fixed to the vertebrae by three fixation screws near the vertices of the triangle. In one specific application, the upper screw is fixed to vertebra L5, while the lower two screws are fixed to vertebra S1. While the plate described herein is particularly useful for application along the anterior aspect of the spinal column in the L5-S1 region, application along the lateral aspects or antero-lateral aspects of the spinal column and also in other regions of the spine is also contemplated.

Figure 2:
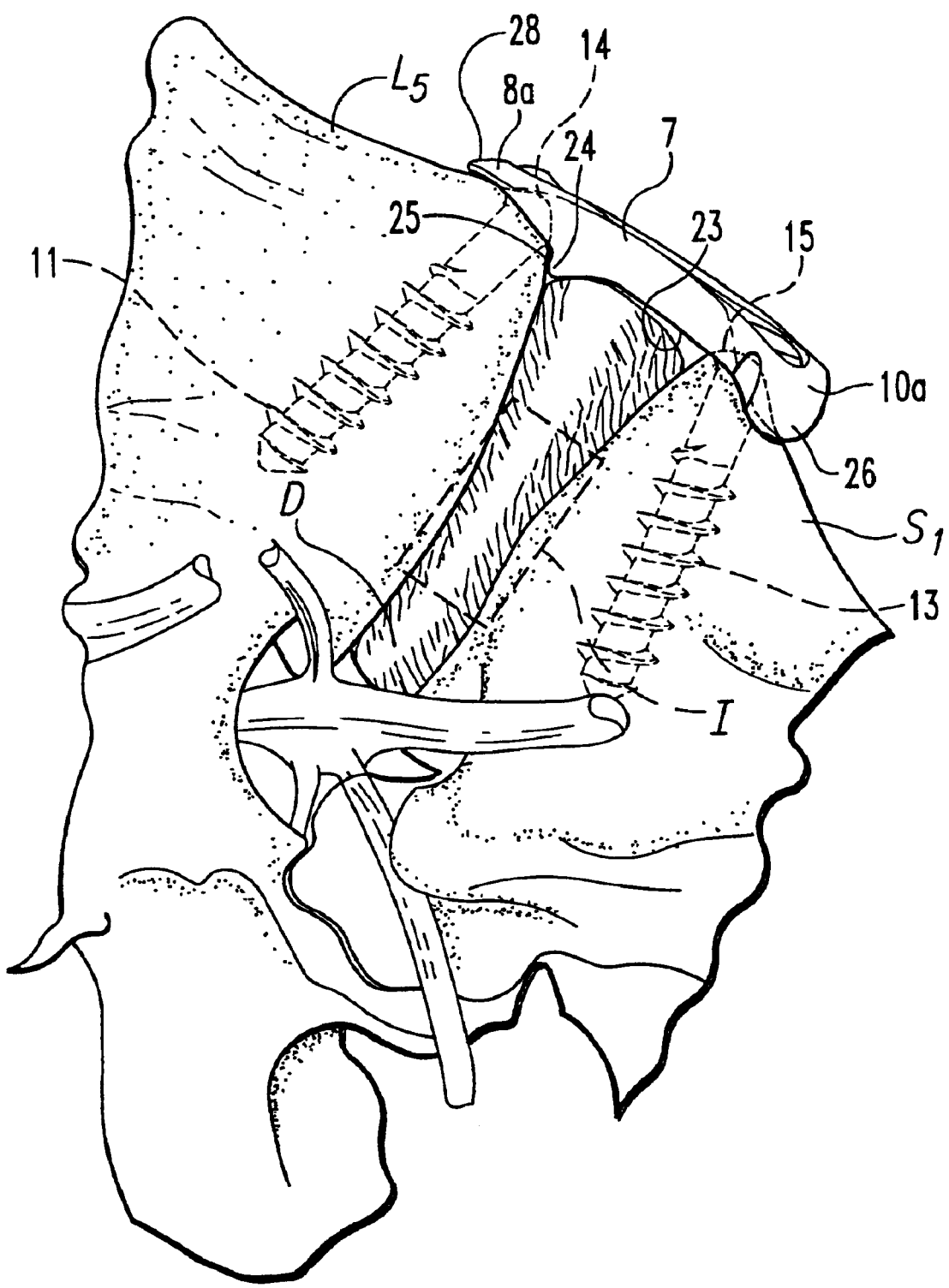
FIG. 2 is a representation of the region and plating system of FIG. 1 viewed in profile.
Figure 3A:
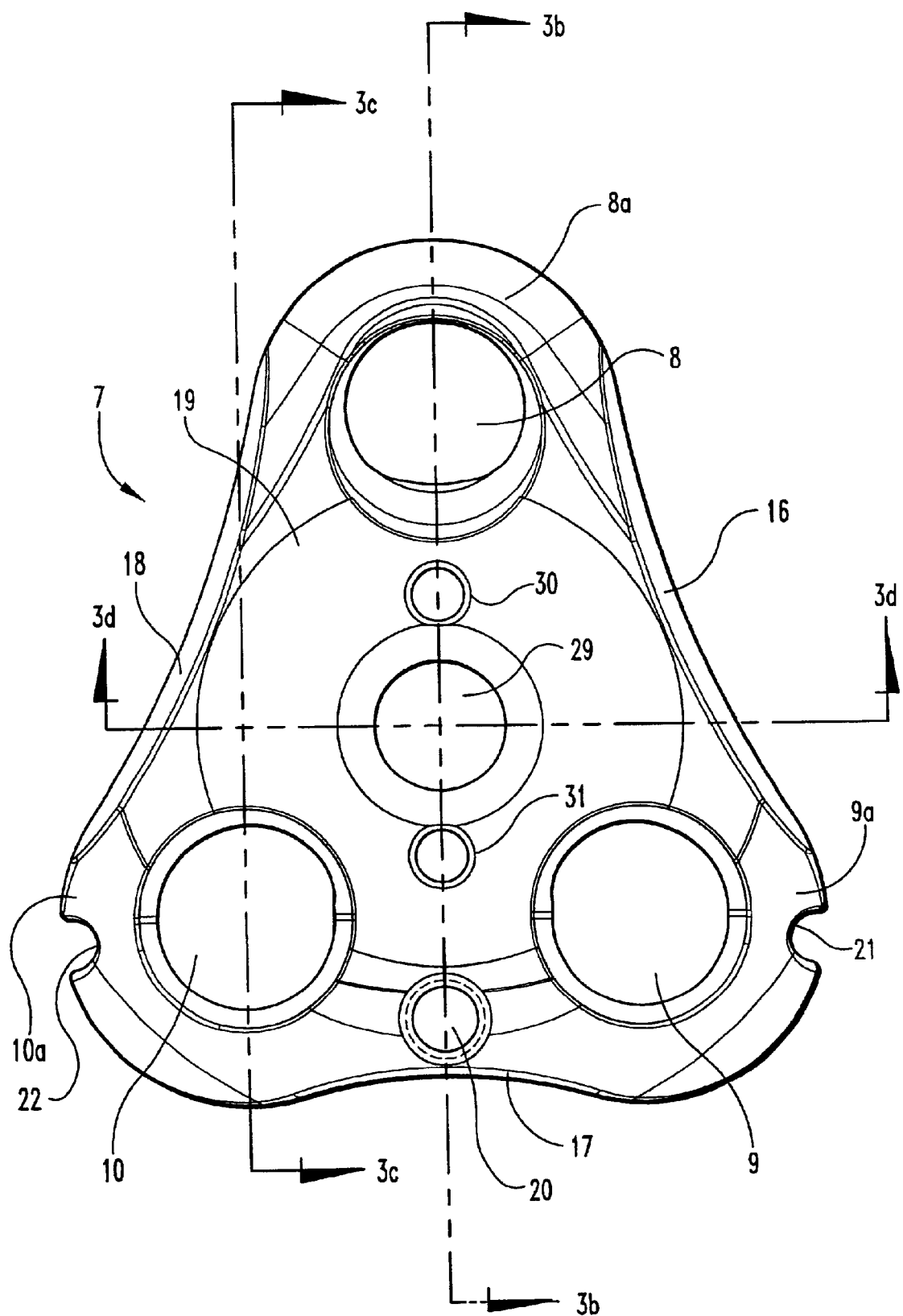

Referring now to FIG. 1, there is a diagrammatic representation of the lumbo sacral region viewed anteriorly. FIG. 1 shows the last lumbar vertebrae L4, L5 and the first sacral vertebrae S1. L4, L5 and S1 are each separated by discs D. The main blood vessels present in this region are also shown, namely the vena cava 1, which divides at L5 into the right iliac vein 2 and the left iliac vein 3, and the aorta 4 which divides at L5 into the right iliac artery 5 and the left iliac artery 6. The space available in the region between the left iliac vein 3 and right iliac artery 5 makes it difficult to secure a conventional plate having appropriate load carrying capabilities to the L5-S1 junction from an anterior approach. The plate 7 according to the invention has a generally triangular shape in order to adapt to the space available for its implantation. Holes 8, 9, 10 are provided in the plate 7 to permit its fixation by means of screws 11, 12, 13 penetrating into the vertebrae L5 and S1. A first hole 8 is formed near the upper vertex of plate 7 in an upper node 8a. Upper node 8a is intended to be placed adjacent vertebra L5 so that screw 11 penetrates into L5 adjacent its lower margin or edge 14, as is illustrated in FIG. 2. The other two holes 9, 10 are formed near the lower vertices of plate 7 in lower nodes 9a and 10a, respectively. Lower nodes 9a and 10a are intended to be placed adjacent vertebra S1 so that screws 12, 13 penetrate into S1 adjacent its upper margin or edge 15, as can be seen in FIG. 2. The vertices of plate 7 are rounded to minimize trauma to adjacent tissue.

The fixation of the screws 11, 12, 13 on the margins 14, 15 of the vertebrae concerned, in orientations defined by the configurations of the holes 8, 9, 10, overcomes the problems associated with the different angulations between these vertebrae. These differences in angulation are related to the differing profiles of the vertebrae. It is further contemplated that the size of plate 7 can be reduced so that it does not extend substantially beyond the margins 14, 15 and the edges of the plate smooth and rounded to minimize trauma when in contact with adjacent tissue. While it is contemplated that the overall configuration of plate 7 can be standardized and provided in a range of sizes, the external dimensions can also vary depending on the patient anatomy determined according to pre-operative modeling of the L5-S1 region for the particular patient.

In one specific embodiment, screws 11, 12, and 13 are cancellous bone screws. It is further contemplates that screws 11, 12, and 13 can be any type of bone engaging fastener known in the art. The underside of the heads of screws 11, 12, and 13 can be rounded above the smooth shank portions of the screws received in the holes 8, 9, and 10. The rounded screw heads allow the screws to become well seated in a curved seating surface formed in plate 7 around holes 8, 9, and 10, thus permitting some angulation of the screws relative to the plate 7 as the screws are installed and tightened in place.

FIGS. 3a–3d show plate 7 in further detail. As illustrated edges 16, 17, 18 of plate 7 are concave to minimize the lateral and caudal extent of plate 7 between nodes 8a, 9a and 10a. Plate 7 can have a shape between edges 16, 17, and 18 that has a slightly concave curvature on its posterior or lower face 23 in order to better adapt to the anatomy of the spinal column and also a slightly convex curvature along anterior or upper face 19 to minimize anterior protrusion. Hole 8 for implantation of screw 11 in L5 is configured to give screw 11 a significant inclination at an angle a relative to the direction perpendicular to anterior face 19 of plate 7. Holes 9, 10 for implantation of the screws 12, 13 in S1 are configured to give screws 12, 13 a substantially perpendicular orientation relative to the anterior face 19 of the plate 7. As discussed above, it is also contemplated that screws 12, 13 can be provided with a head having a spherical lower bearing surface so that screws 12 and 13 can assume any one of multiple angular orientations with anterior face 19. Plate 7 also includes near its lower edge 17 an opening 20 and near its lower nodes 9a and 10a indents 21 and 22, respectievly. Opening 20 and indents 21, 22 are intended to allow the plate 7 to be gripped by means of a tool adapted for this purpose, it being understood that hole 20 and indents 21 and 22 constitute only one particular example of such means which can cooperate with a gripping tool. Examples of such a tool will be described below.

Posterior face 23 of plate 7 is intended to be directed towards the vertebrae. Posterior face 23 has a protrusion 24 extending along at least part or substantially all of its width. Protrusion 24 has an upper face 25 that is positioned and configured to bear against the lower lip of the anterior margin 14 of the lower endplate of L5, as can be seen in FIG. 2. The oblique orientation of screw 11 tends to press protrusion 24 against L5, which strengthens the hold of plate 7 on L5 and resists any pivoting effect of plate 7 about screw 11 that may result upon lateral flexion of the spine. As is shown, plate 7 also includes protrusions 26, 27 on its posterior face 23 in the area of lower nodes 9a, 10a, along the edges of plate 7. Protrusions 26, 27 are placed along S1 and bear against the anterior face of S1 adjacent margin 15, as can be seen in FIG. 2, so as to help hold plate 7 in place. The anchoring of plate 7 on L5 can also be complemented by a ridge-shaped upper lip 28 (FIGS. 3b and 3c), or by one or more points 734 (FIG. 23), formed adjacent edges 16, 18 and extending from posterior face 23 of the plate 7 in the region of upper node 8a in the area of its contact with the anterior face of L5.

Plate 7 also includes a central opening 29 intended to permit insertion and securement of a retaining element for blocking screws 11, 12, 13 inserted through holes 8, 9 and 10, respectively. Plate 7 includes two openings 30, 31 cooperating with the retaining element. The function of the retaining element is to prevent screws 11, 12, 13 from tending to escape from their receiving seat after they have been tightened onto plate 7.

Figure 5:
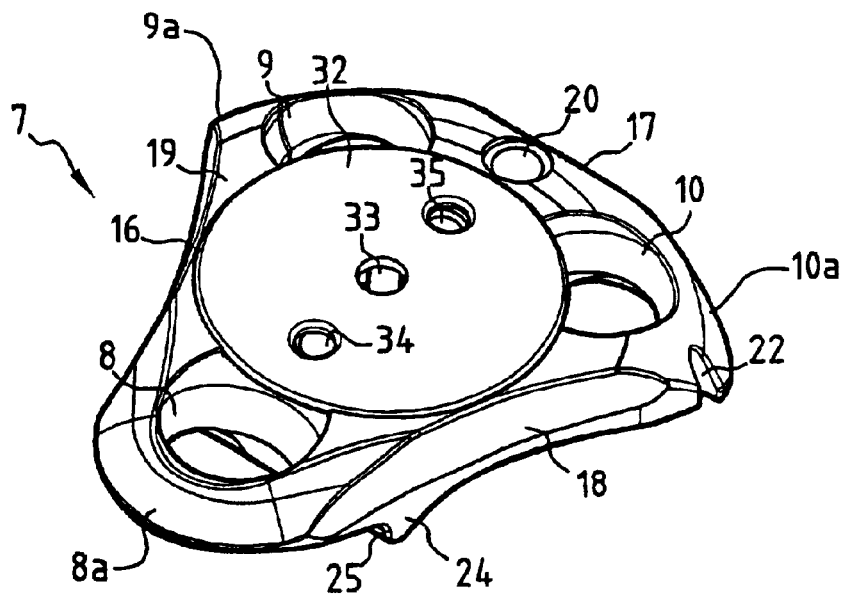
FIG. 5 is a perspective view of a plate according to the present invention equipped with one embodiment of a retaining element.
Figure 6:
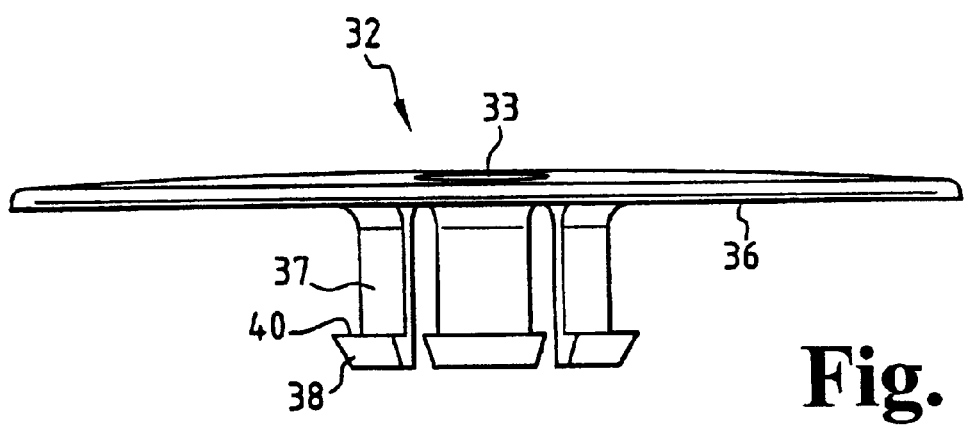
FIG. 6 is a side view of the retaining element on the plate of FIG. 5.

FIG. 5 shows a plate 7 identical to that in FIG. 3, equipped with a first example of a retaining element 32. Retaining element 32 has a circular or substantially circular shape, the diameter of which allows retaining element 32 partially covers holes 8, 9, 10 after screws 11, 12, 13 are inserted. Retaining element 32, also shown in FIG. 6, includes a central opening 33 and two openings 34, 35 situated on either side of central opening 33. Openings 34, 35 correspond in location to openings 30, 31 of plate 7. Retaining element 32 includes a lower face 36 that includes extending therefrom a series of elastic tabs 37 distributed about central opening 33. It is contemplated that at least two or more tabs 37 are provided. The lower end of each tab 37 includes a beveled end 38 and a bearing surface 40.

After fixation of plate 7 to the vertebrae, retaining element 32 can be put into place on plate 7 in the following way. Using a suitable tool that includes two rods penetrating openings 34, 35 of retaining element 32, retaining element 32 is brought into position toward plate 7, and the ends of the rods are introduced into openings 30, 31 of plate 7. Retaining element plate 32 is then pushed against plate 7 so as to introduce elastic tabs 37 into central opening 29 of plate 7. Beveled ends 38 facilitate this introduction and deflect tabs 37 inwardly toward one another during this introduction. Tabs 37 are thus fitted in central opening 29 of plate 7 and prevent retaining element 32 from becoming dislodged from plate 7. A bearing surface 39 (FIG. 3b, 3d) is formed in central opening 29 of plate 7 to cooperate with bearing surface 40 formed on beveled end 38 of each tab 37. Retaining element 32 can thus be installed by clipping it onto plate 7, and can be dislodged therefrom using a suitable tool that can pry tabs 37 from hole 29. It should be understood that other techniques for positioning retaining element 32 on plate 7 are also contemplated, including simply manually placing tabs 37 in hole 29. Another embodiment of the plate of the present invention is provided in FIG. 4. Plate 107 is generally identical to plate 7 discussed above except as otherwise noted below. Plate 107 includes holes 109, 110 that have an oblong shape so as to give the surgeon more freedom for the location of implantation of screws 12, 13 in S1. Oblong holes 109, 110 further allow plate 107 to adapt to the postoperative changes in the morphology of the patient. However, in the FIG. 4 embodiment hole 108 that receives screw 11 implanted in L5 has a shape exactly adapted to that of the head of screw 11 and prohibits any relative displacement between plate 107 and screw 11 at this level to provide good stability for the implanted plate 107

Figure 7B:
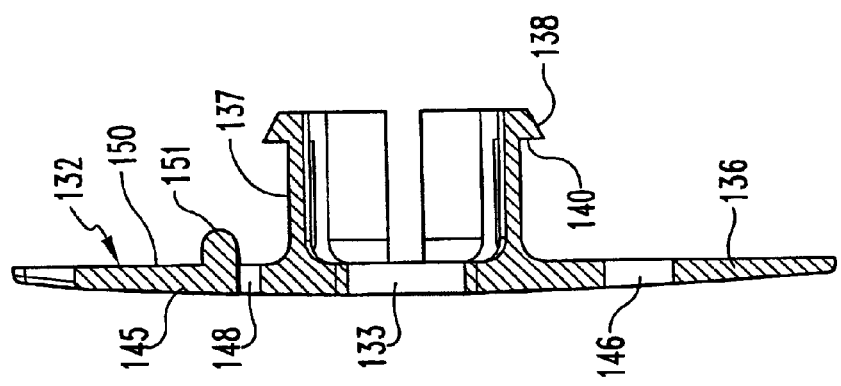
FIGS. 7a and 7b show, respectively, a plan view and a view in cross section along 7b–7b of FIG. 7a of another embodiment retaining element.
Figure 7A:
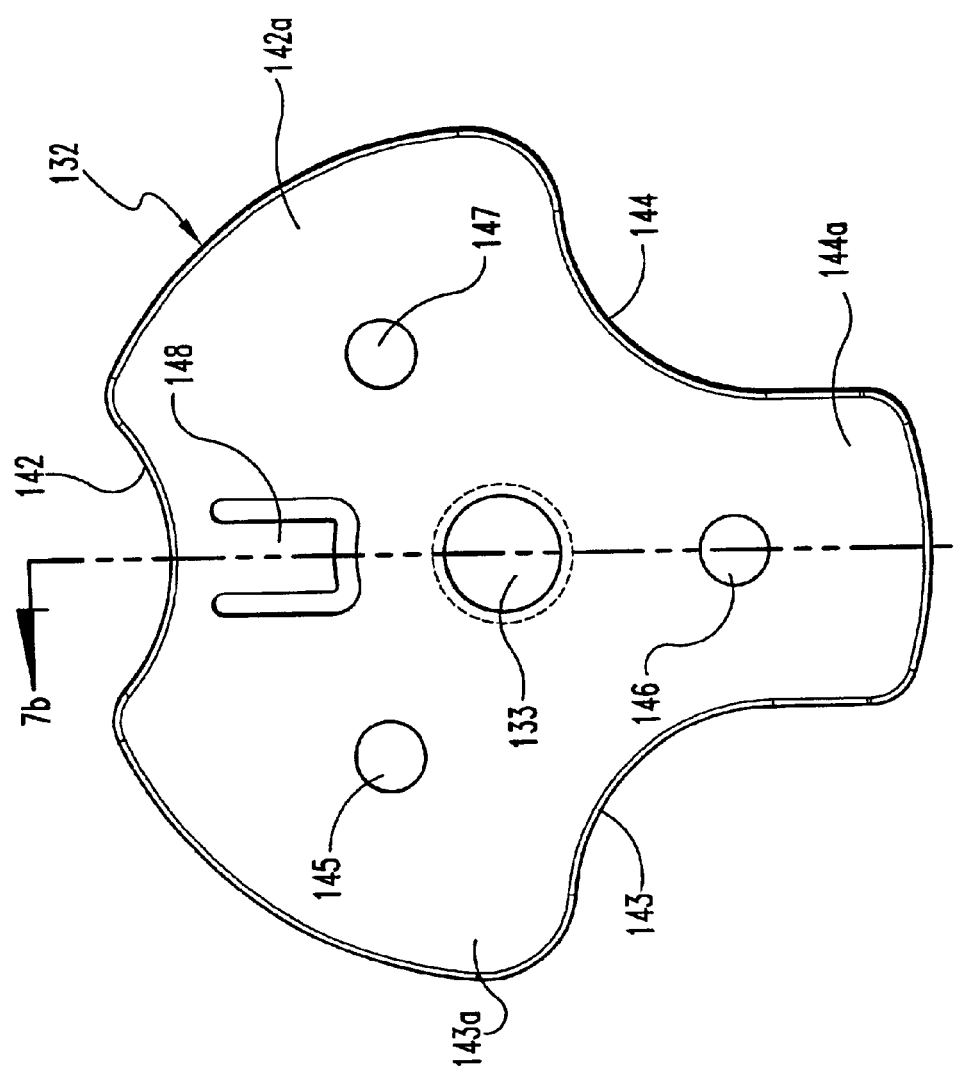

Another embodiment retaining element is shown in FIGS. 7a and 7b. Retaining element 132 is not circular here but has on its periphery three cutouts 142, 143, 144 that form flange like projections 142a, 143a and 144a. Like retaining element 32, retaining element 132 includes a lower face 136, a central opening 133, and elastic tabs 137 about central opening 133 with beveled ends 138 and bearing surfaces 140. To facilitate rotation with a tool, three openings 145, 146, 147 are formed on retaining element 132, offset 120° relative to one another about central opening 133. A U-shaped opening 148 is also formed in order to define an elastic tongue 149 that lifts when a force is exerted on its posterior face 150. The end of the tongue 149 has a stud 151 on its posterior face.

Figure 4:
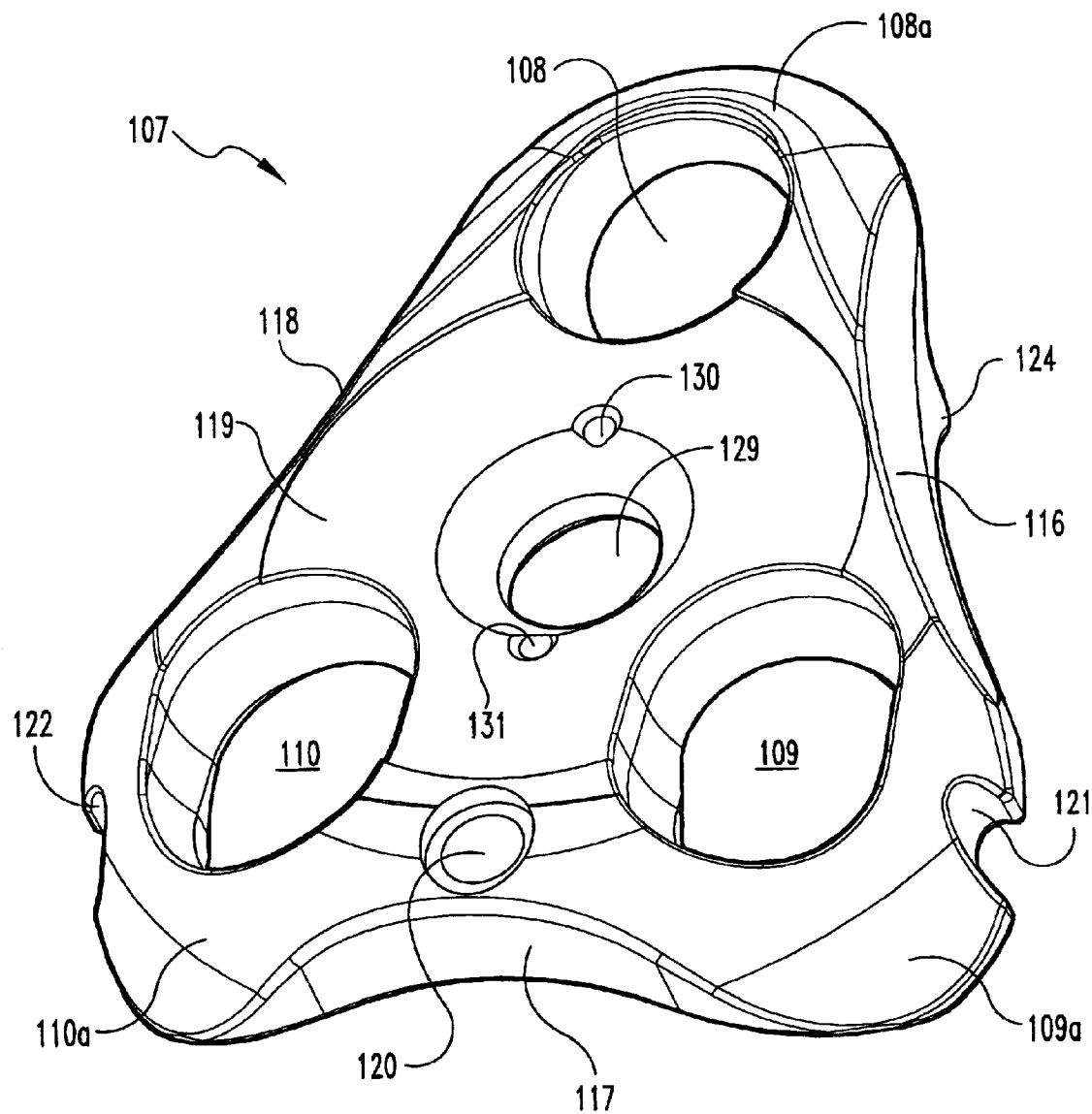
FIG. 4 is a perspective view of another embodiment of a plate according to the present invention.
Figure 8A:
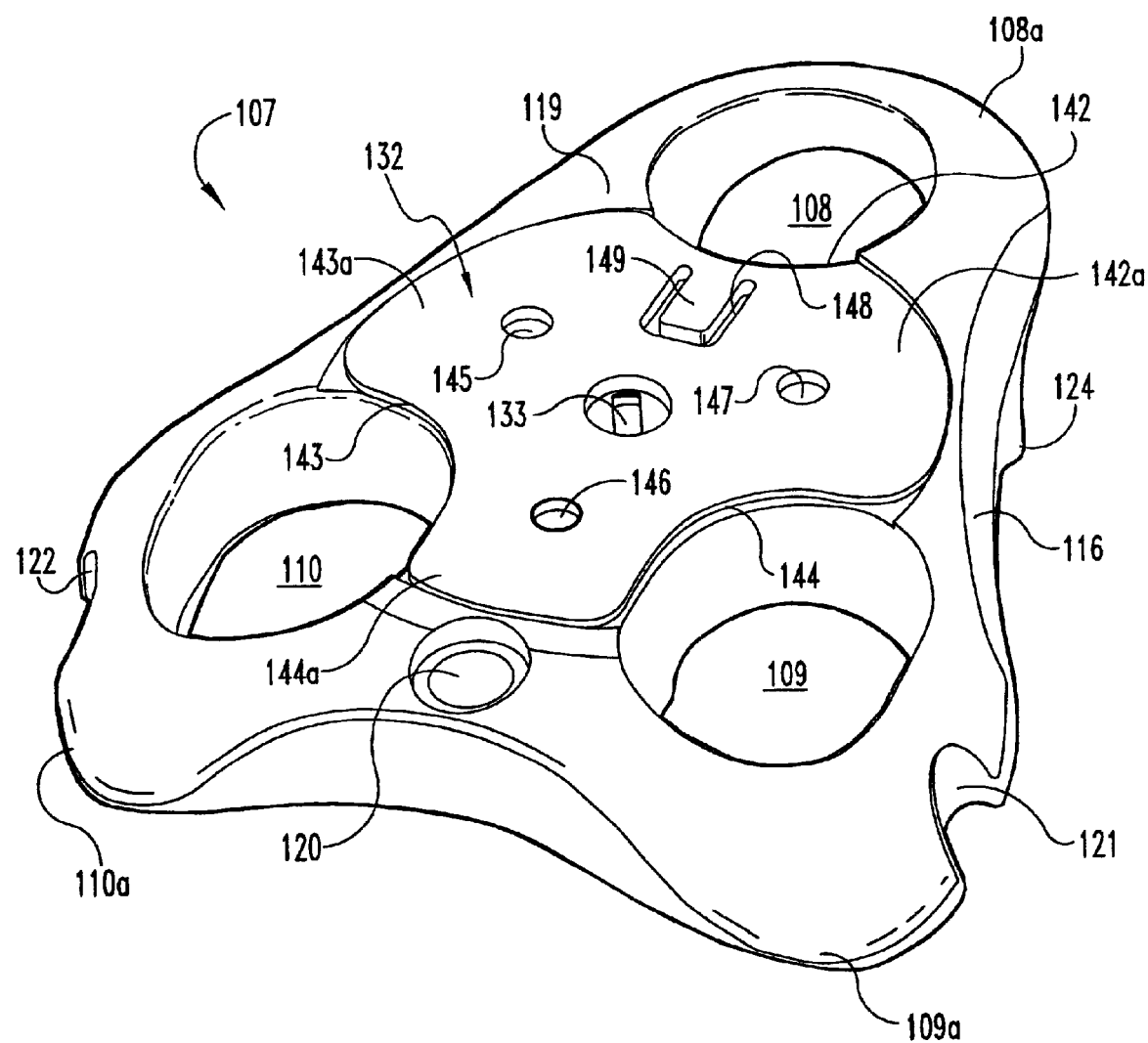
FIGS. 8a and 8b are perspective views of a plate according to the invention equipped with a retaining element according to the example in FIG. 7, the retaining element being either in a non-retaining position (FIG. 8a) or in a retaining position (FIG. 8b)
Figure 8B:
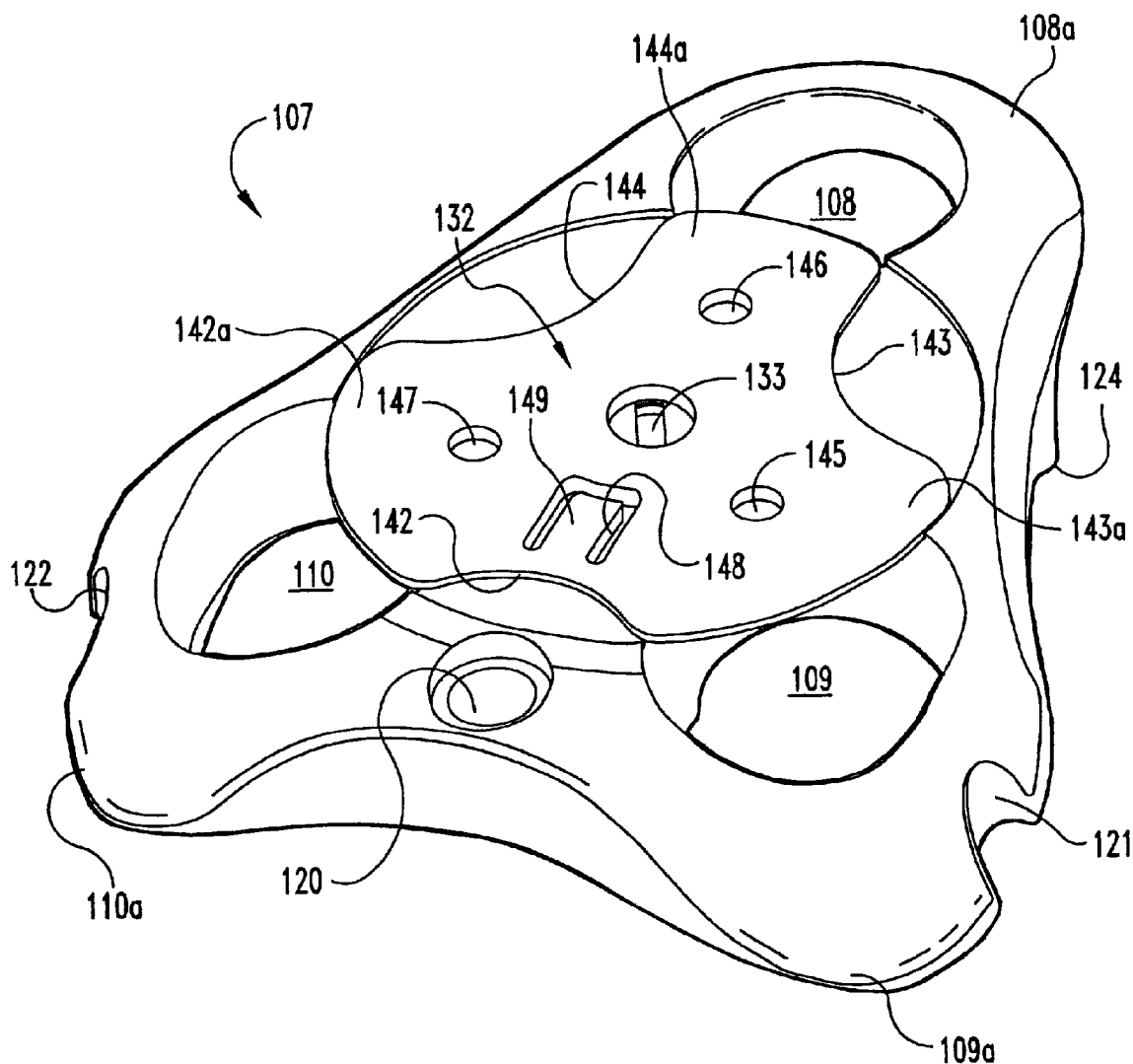

Retaining element 132 is used as follows. Referring to FIGS. 8a and 8b, retaining element 132 can be placed on plate 107 before screw insertion. Retaining element 132 is initially placed on plate 107 so that cutouts 142, 143, 144 leave holes 108, 109, 110 of plate 107 entirely exposed, as shown in FIG. 8a, permitting insertion and tightening of screws 11, 12, 13 upon positioning of plate 107 on the vertebrae. The positions and dimensions of cutouts 142, 143, 144 are chosen accordingly. With retaining element 132 in this position, stud 151 of tongue 150 is engaged in a receiving seat 131 (FIG. 4) formed on anterior face 119 of plate 107. Plate 107 is then put into place and screws 11, 12, 13 are tightened. A suitable tool is then inserted in one or more of openings 145, 146, 147 of retaining element 132, and retaining element 132 is turned 180° with the aid of this tool. Under the effect of the force applied to it, stud 151 is released from its seat and permits rotation of retaining element 132. Consequently, flanged portions 142a, 143a, 144a of retaining element 132 partially cover holes 108, 109, 110 as shown in FIG. 8b. Retaining element 132 thus prevents screws 11, 12, 13 from backing out beyond anterior face 119. Retaining element 132 is held in this position by virtue of the engagement of stud 151 in a receiving seat 130 (FIG. 4.) The pre-fitting of retaining element 132 on plate 107 prior to positioning plate 107 on the vertebrae of the patient eliminates the fiddle factor for the surgeon.

Plate 107 of the osteosynthesis device in FIG. 8 has oblong holes 109, 110, but it is understood that retaining element 132 can also be used on plate 7 which has circular holes 9, 10. Those skilled in the art will readily appreciate that the clippable retaining elements 32, 132 described above can have different configurations than those shown herein and still block screws seated in the plate holes.

Figure 9:
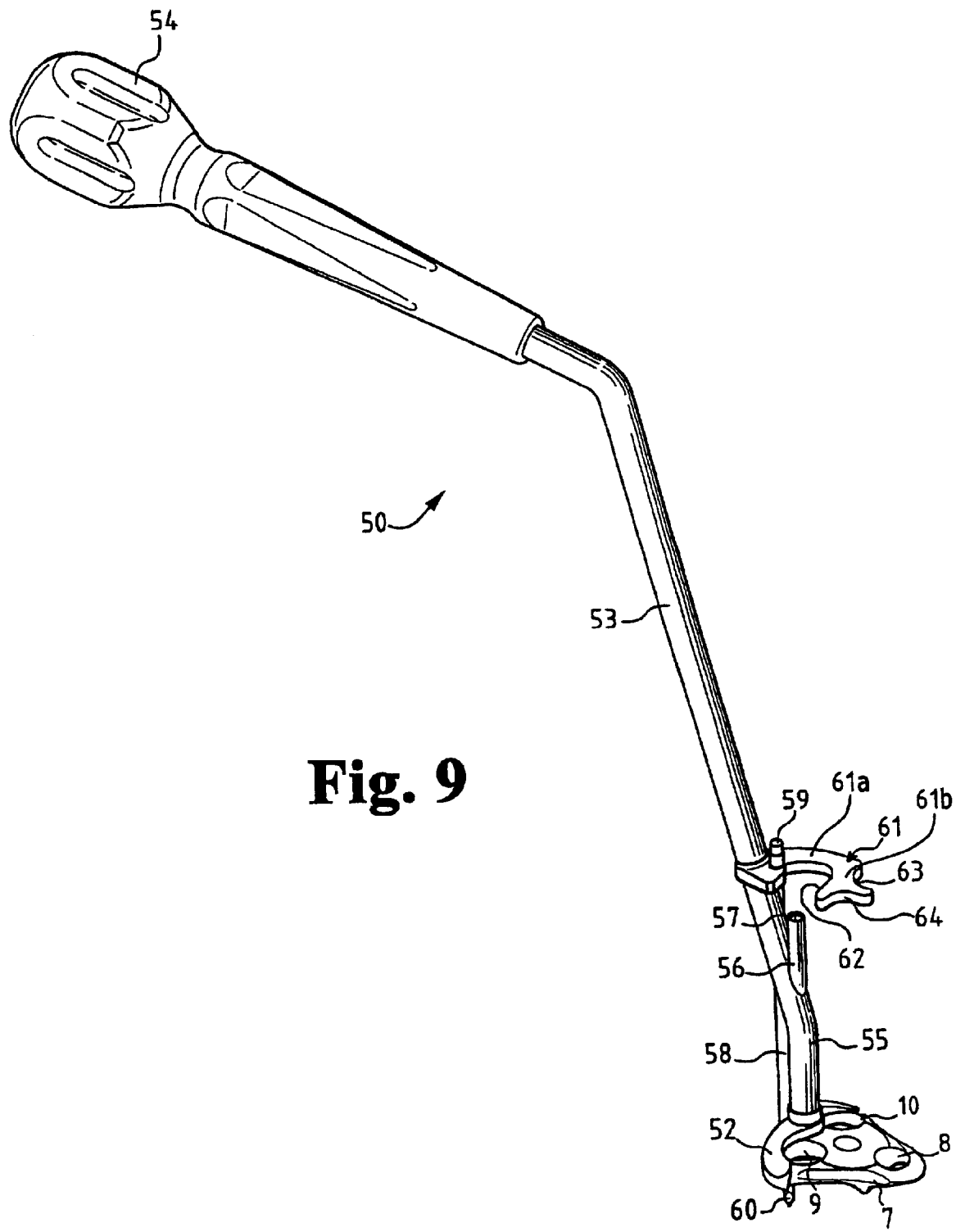
FIG. 9 is a perspective view of a tool which can be used for securing a plate of the present invention to the L5-S1 region.
Figure 10:
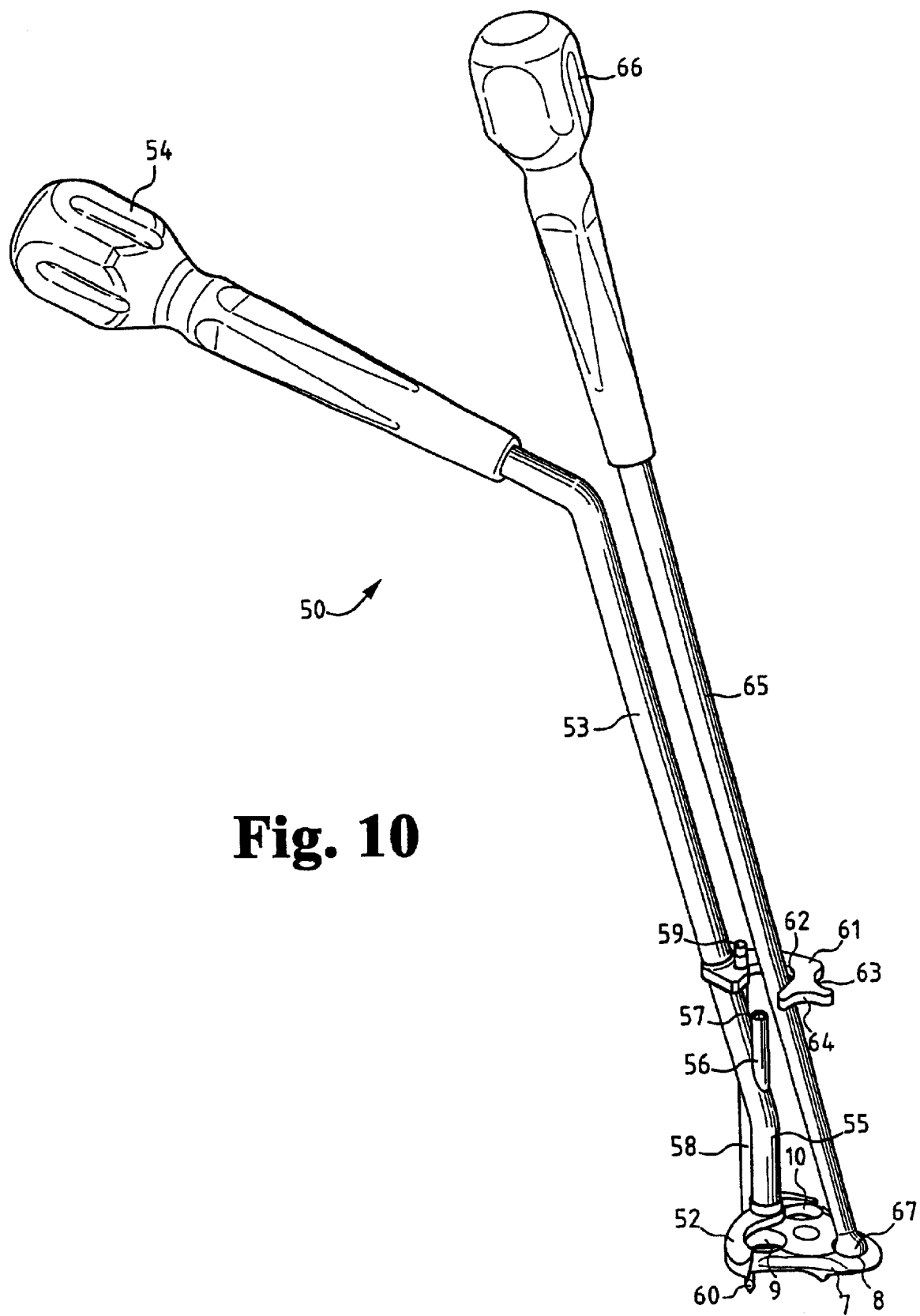
FIG. 10 shows the tool from FIG. 9 equipped with a pusher which can be used during fitting of the plate.
Figure 11:
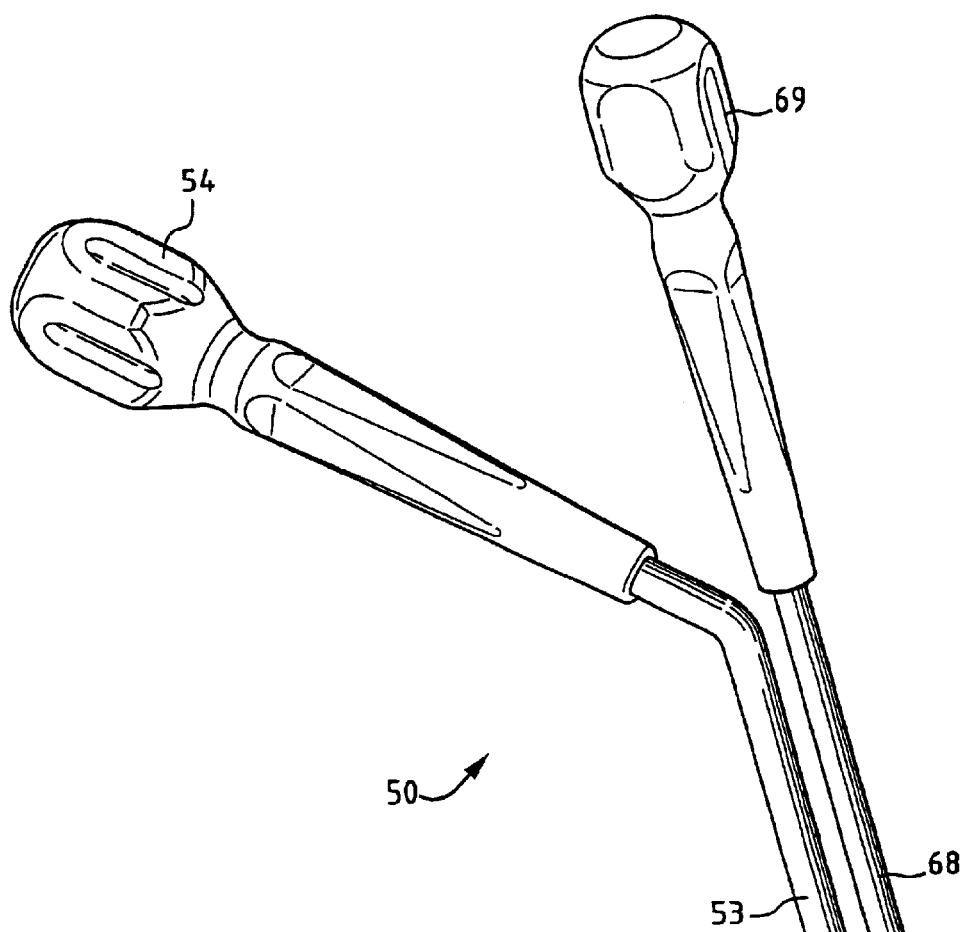
FIG. 11 shows the tool from FIG. 9 equipped with a rod for drilling holes into the vertebrae which will accommodate the screws for fixing the plate.

The present invention also includes an instrument designed for positioning the plates and screws of the present invention as shown in FIGS. 9–11. Instrument 50 will be described with respect to plate 7, it being understood that instrument 50 has application with the other plate embodiments described herein.

Instrument 50 includes a plate holding portion 52 which matches the shape of lower edge 17 of plate 7. Holding portion 52 includes studs (not shown) that are inserted into indents 21, 22. It is further contemplate that holding portion 52 and plate 7 can be provided with any other means of establishing a defined relative position therebetween. Instrument 50 further includes a shaft 53 which is bent and has a grip 54 at its proximal end to allow the surgeon to manipulate instrument 50 and plate 7. Shaft 53 has adjacent its distal end a distal portion 55 perpendicular to anterior surface 19 that supports holding portion 52.

It is contemplated that at least distal portion 53 is hollow, and instrument 50 further includes a rod 56 extending through the hollow distal portion 55 of shaft 53. Rod 56 can be provided with threads and held on shaft 53 by a corresponding thread on an inner wall surface of shaft 53. The distal end of rod 56 lodges in opening 20 of plate 7. The inner wall surface of opening 20 can include a thread corresponding to a thread on the lower end of rod 56. The proximal end of rod 56 opens to the outside of shaft 53 and has a recess 57 for insertion of a screwdriver. Tightening and loosening rod 56 makes it possible for plate 7 and holding portion 52 to be connected and disconnected.

Instrument 50 also includes a tube 58 which can pass through shaft 53 and is connected to it. Tube 58 has an inner passage that allows a rod 59 to be inserted therein and held in position in its internal space. Rod 59 includes at its lower end a point 60 which bears on or embeds in vertebra S1 upon positioning of plate 7 thereon. Instrument 50 further includes a support 61 attached to shaft 53 and arranged substantially horizontally. Support 61 includes a lateral arm 61a extending to a guide member 61b that includes three guiding portions 62, 63, 64. First guiding portion 62 is formed on the side of guide member 61b adjacent shaft 53 and second and third guiding portions 63 and 64 are formed on the side of guide member 61 opposite shaft 53.

Use of instrument 50 to secure plate 7 will now be described. In a first step, plate 7 is fixed on holding portion 52 as described above. The surgeon then positions plate 7 on L5 and S1 at the desired site. Plate 7 can be held at the desired site by penetrating point 60 of rod 59 into S1. Pusher 65, as shown in FIG. 10, is also used to firmly seat plate 7 on L5 and S1. Pusher 65 is a shaft which has at its proximal end a grip 66 and at its distal end a bulb 67 which can lodge in hole 8 of plate 7. Bulb 67 could also lodge in a depression or a hole provided in plate 7 specially adapted for this purpose. Bulb 67 can be replaced by any other means capable of ensuring its function of maintaining the position of pusher 65 bearing on plate 7.

In a second step, pusher 65 is withdrawn and the holes intended to receive screws 11, 12, 13 are drilled in L5 and S1. This drilling is carried out, as is shown in FIG. 11, using a drill rod 68. Drill rod 68 includes at a proximal end a grip 69 and at a distal end a bit 70 capable of drilling a hole in a vertebra to receive a screw. To drill a hole in L5 , as is shown in FIG. 11, drill rod 68 is guided through hole 8 of plate 7, and applied against guiding portion 62 of support 61. The position of support 61 and the shape of guiding portion 62 are determined in such a way that the angle of penetration of the drill tip in L5 corresponds to the desired angle of penetration of screw 11. Once the hole in L5 is completed, the holes in S1 for receiving screws 12, 13 are then drilled in a similar manner. The drill rod, however, is oriented away from grip 54 in order to provide the appropriate caudal orientation of screws 12 and 13. Drill rod 68 is then guided through hole 9 and guiding portion 63 of support 61, and through hole 10 and guiding portion 64 of support 61 to drill holes in S1.

Finally, screws 11, 12, 13 are inserted in the holes which have just been drilled and are tightened by means of a conventional screwdriver, which can also be applied against support 61 in a manner similar to what was done for drill rod 68. Plate 7 is then disconnected from holding portion 52 by loosening rod 56. The procedure is completed by putting into place a retaining element to block screws 11, 12, 13, if such a retaining element were provided.

It is contemplated that holding portion 52 can be detachable from shaft 53 to allow the use different sizes of plate holding portions 52. Various holding portions 52 can be provided that are based on various external dimensions of different sized plates 7. Likewise, for the optimum choice of the points of penetration and the values of the angles of penetration of screws 11, 12, 13, the position and orientation of support 61 and its guiding portions can be determined and adjusted by the surgeon before and during the procedure.

Figure 12:
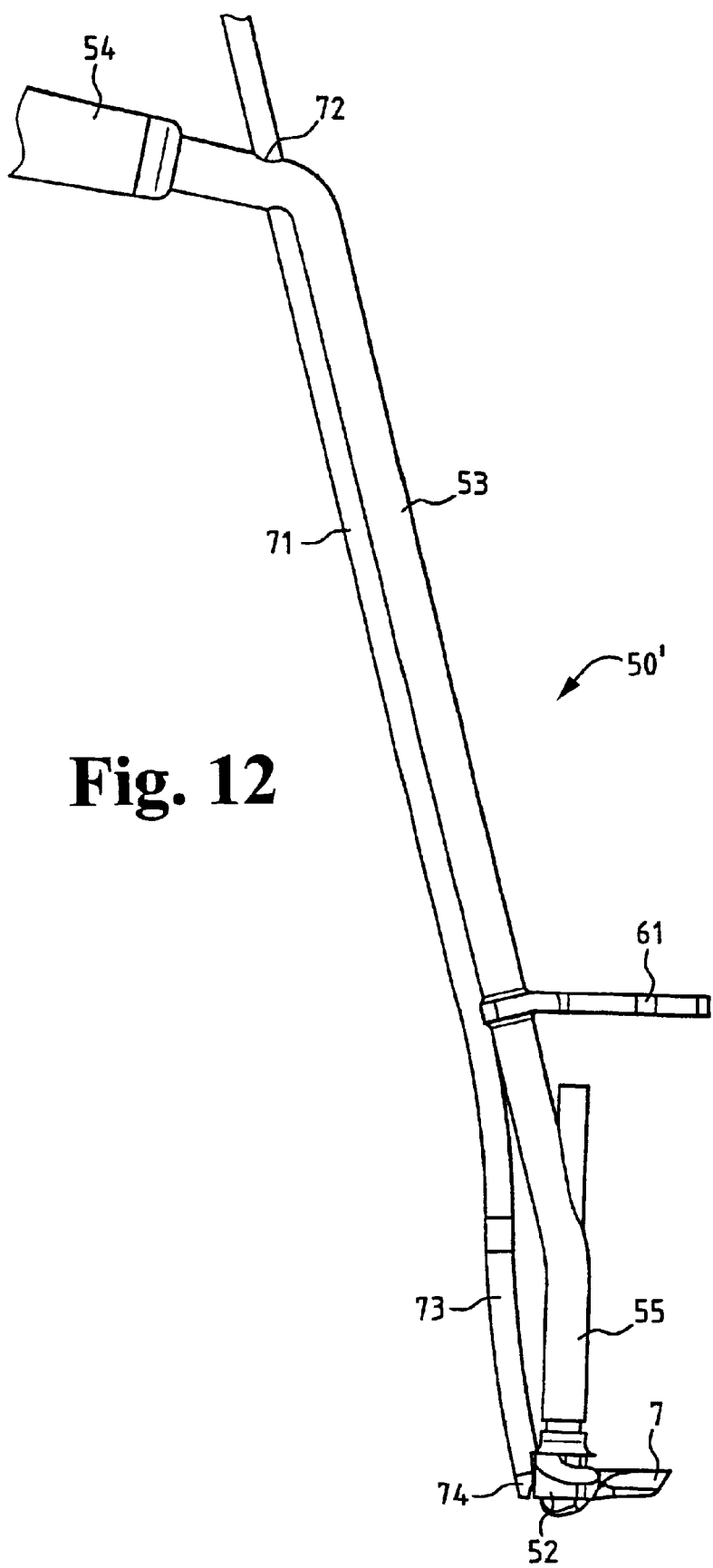
FIG. 12 shows a side view of another embodiment of the tool of FIG. 9.

Another embodiment of instrument 50 is shown in FIG. 12 and designated as 50'. The elements of instrument 50' common to instrument 50 are designated therein by the same reference numbers. In this embodiment, tube 58 and rod 59 are replaced by a flexible rod 71 arranged along shaft 53 and passing through its proximal end via a hole 72. At the distal end of flexible rod 71 there is a rigid rod 73 which ends in a bearing surface 74 that will rest on S1 upon positioning of plate 7 at a suitable angle therewith. Flexing of rod 71 provides an indication to the surgeon when such contact between bearing surface 74 and S1 is made.

Figure 13:
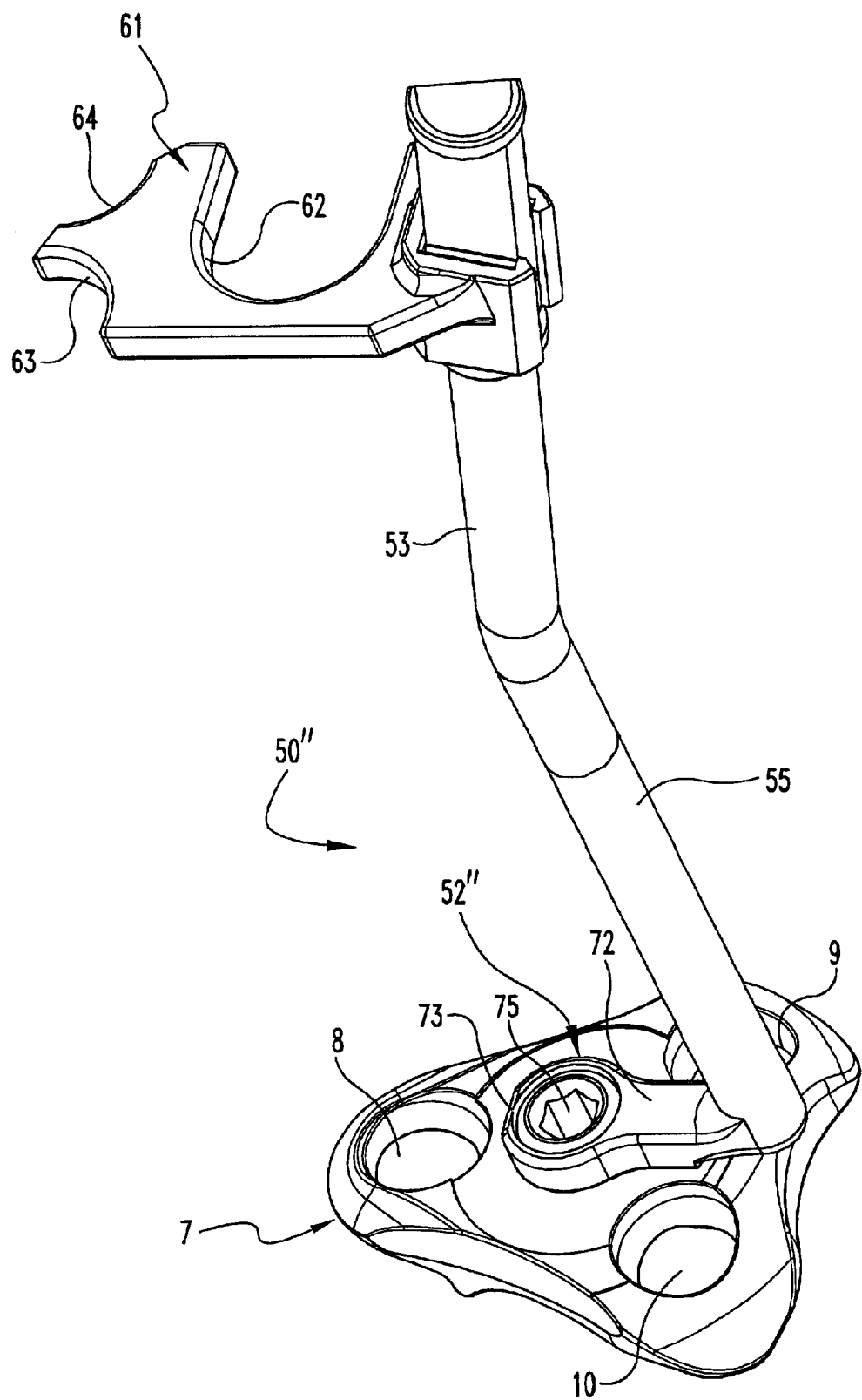
FIG. 13 is a perspective view of another embodiment of a tool which can be used for securing a plate of the present invention to the L5-S1 region.

It will be understood that variants in the details of the design of instrument 50 described herein are contemplated. For example, the means for connecting and disconnecting plate 7 and holding portion 52 can be different than those described. It is possible to use, for example, an instrument in which the distal end of rectilinear portion 55 of shaft 53 can be clipped/unclipped to cooperate with hole 20 of plate 7. For example, as shown in FIG. 13, instrument 50", except as otherwise noted, is the same as instrument 50 and like elements are designated with the same reference numerals. Instrument 50" includes a plate holding portion 52" that includes a foot 72 having a hole 73 therethrough. A fastener 75 extends through hole 73 and engages foot 72 to hole 29 of plate 7. Foot 72 can include a stud (not shown) extending downwardly therefrom that is positionable in hole 20 to prevent rotation of plate 7 about fastener 75. With instrument 50 plate 7 need not include indents 21, 22, although provision of the same is not precluded.

Figure 14A:
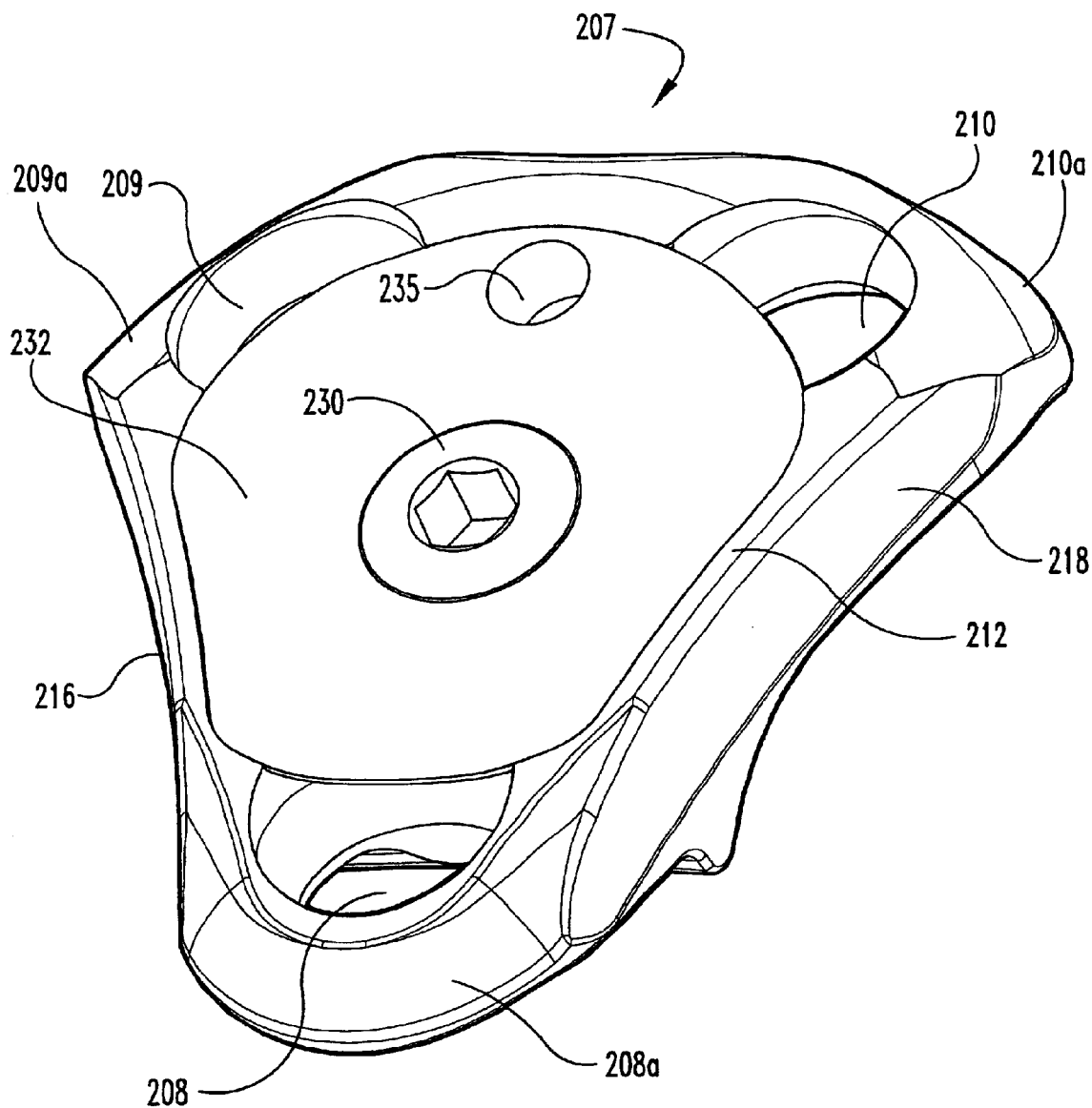
FIG. 14a is a perspective view of a plate according to the present invention equipped with another embodiment retaining element
Figure 14B:
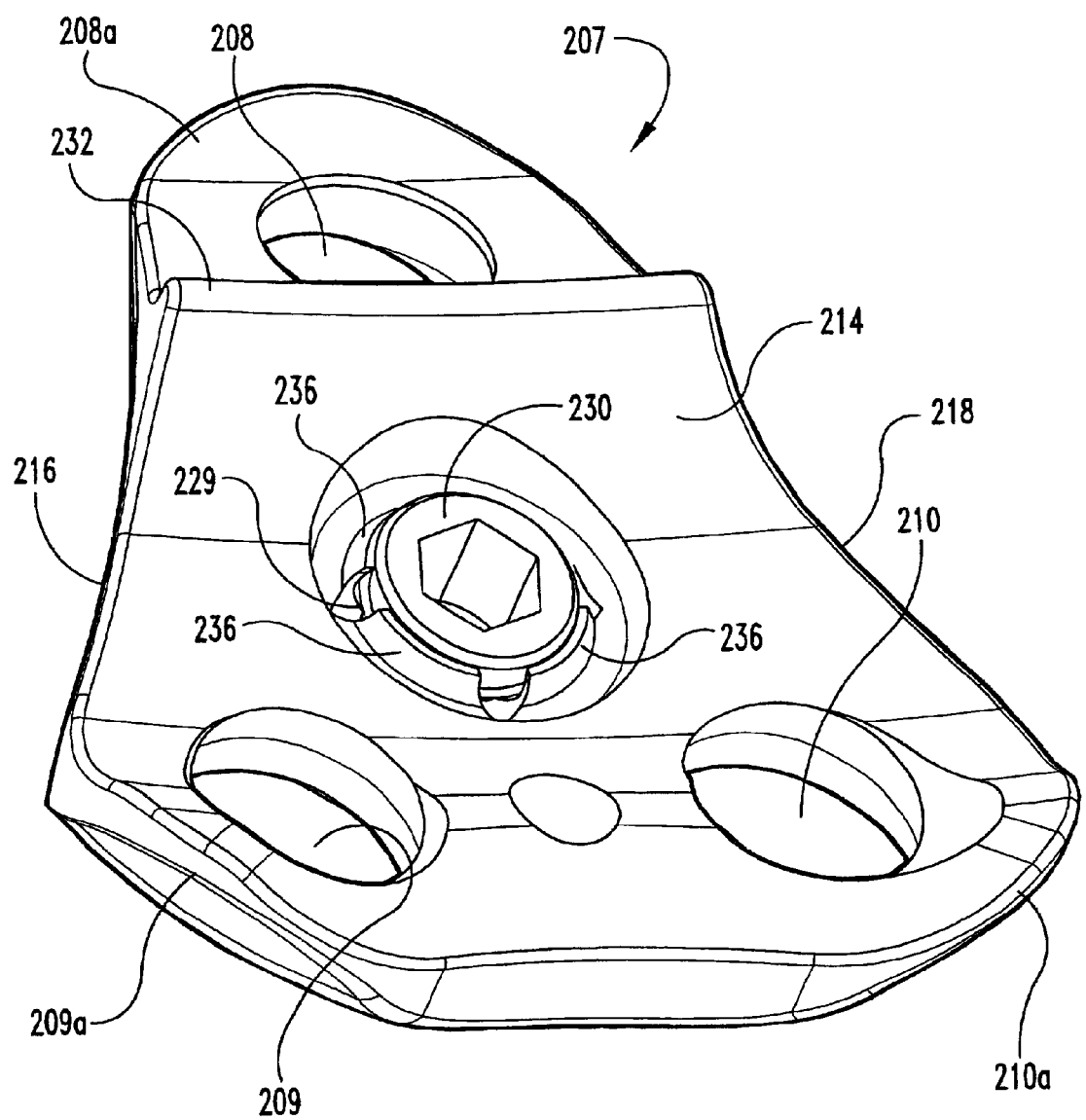
Figure 16:
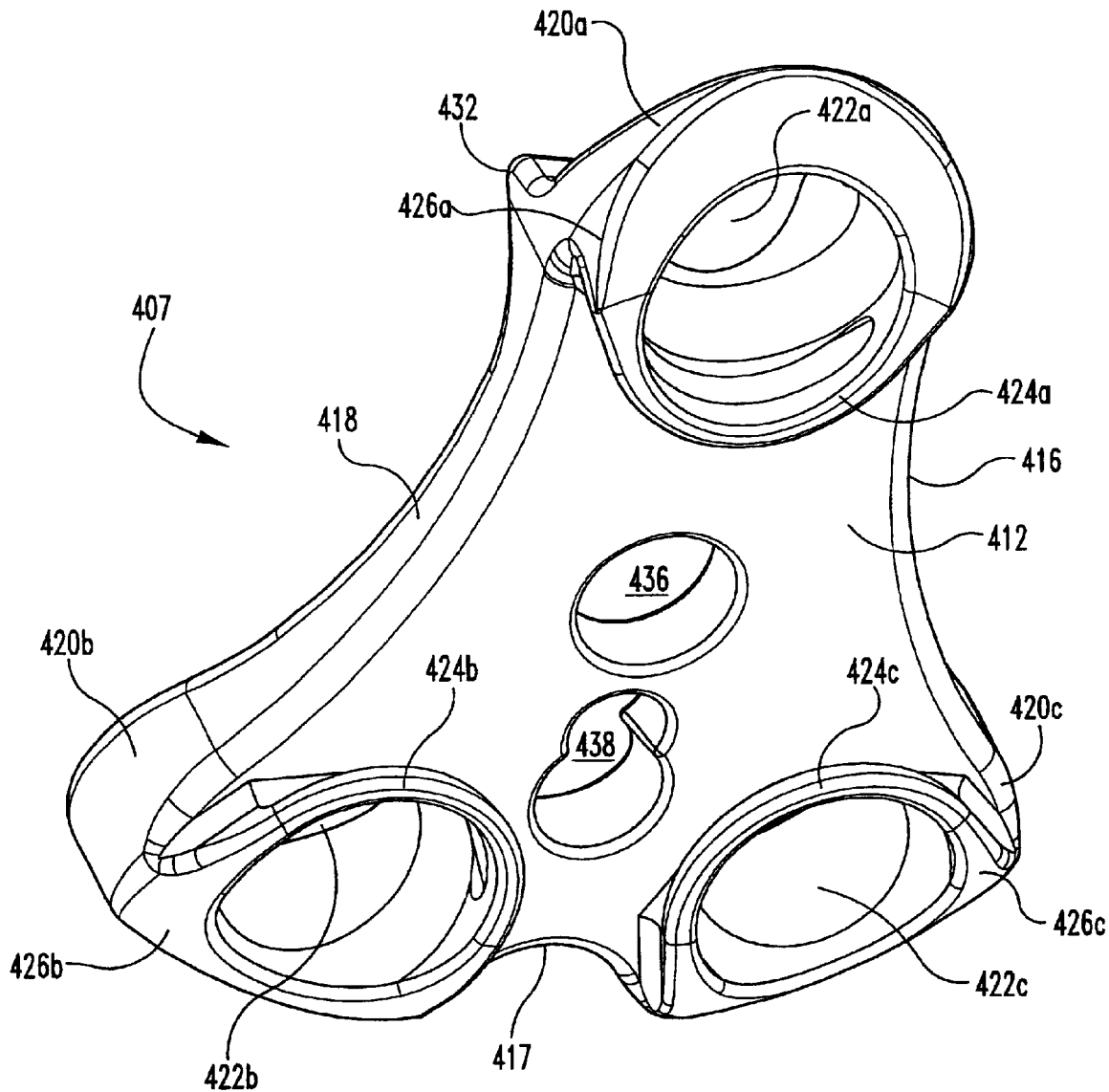
FIG. 16 is a perspective view of another embodiment plate according to the present invention.
Figure 17:
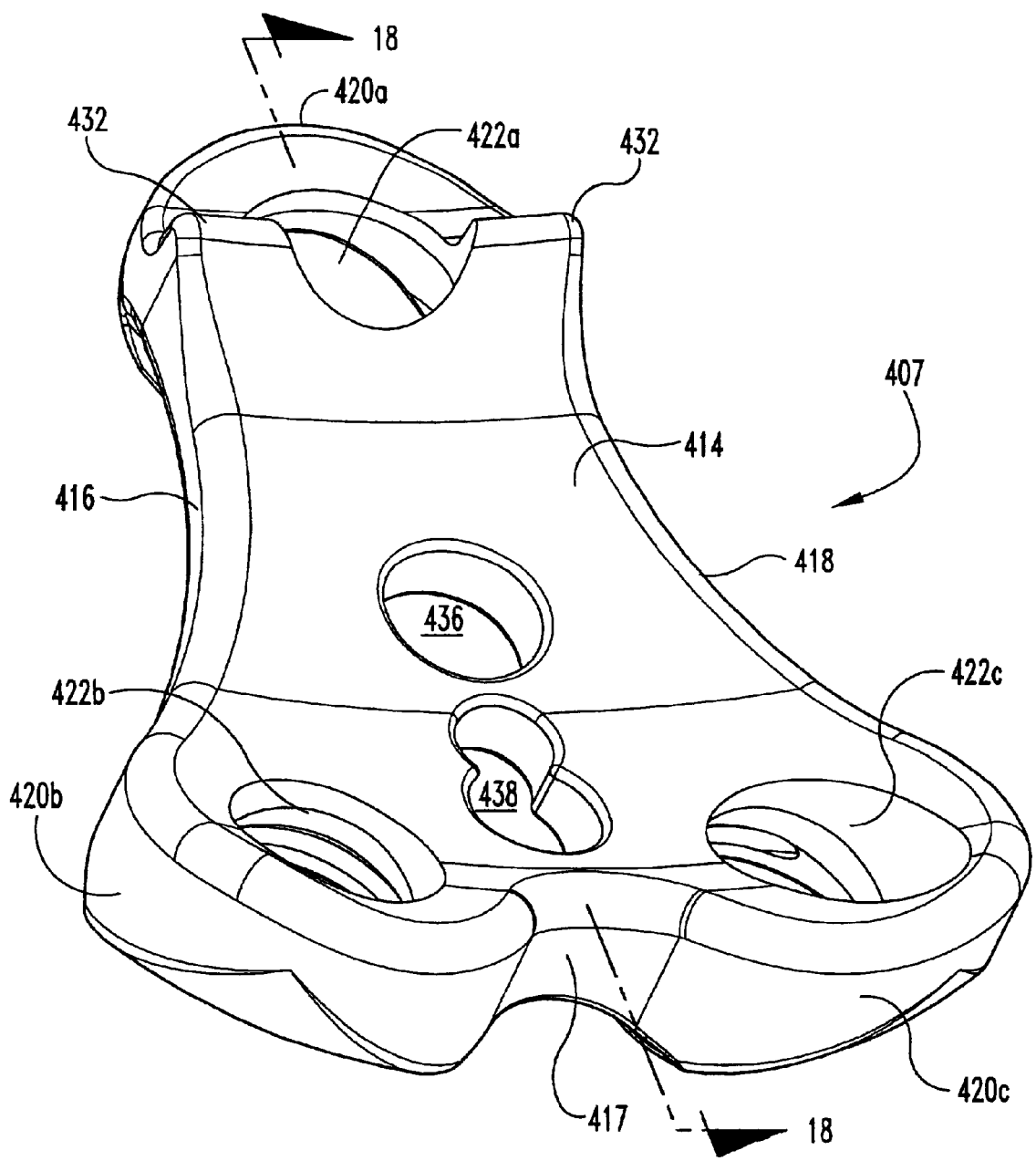
FIG. 17 is a perspective view of the posterior side of the plate of FIG. 16.

Referring now to FIGS. 14a–14b, another embodiment plate 207 is shown. Plate 207 is identical to plates 7, 107 except with respect to its retaining element 232, and that plate 207 does not include indents for coupling to a plate holder, although the provision of such indents is not precluded. Plate 207 includes upper hole 208 extending through upper node 208a, first lower hole 209 extending through first lower node 209a, and second lower hole 210 extending through second lower node 210a. Plate 207 includes edges 216, 217, 218 extending between anterior face 212 and posterior face 214. A retaining element 232, shown in further detail in FIGS. 15a–15b, is secured to anterior face 212 of plate 207 and partially overlaps holes 208, 209, 210 when screws 11, 12 and 13 are positioned therein.

Retaining element 232 is secured to plate 207 by a locking fastener 230 that threadingly engages a central hole 229 of plate 207. Retaining element 232 has a generally triangular shape with rounded apices that generally match the outer edge profile of plate 207. Retaining element 232 can include a hole 235 that can be used to assist in placing locking element 232 to its proper positioning on anterior face 212 or to hold retaining element 232 in position as locking fastener 230 is threaded into hole 229. Locking fastener 230 engages a central hole 238 of retaining element 232 and contacts lip 239 extending therearound to hold it against anterior face 212. As shown in FIG. 14b, locking fastener 230 also extends through hole 229 to posterior face 214. Hole 229 has inwardly biased tangs 236 extending therearound at its lower opening, which can be recessed with respect to posterior face 214. Tangs 236 clamp onto locking fastener 230 and prevent it from unthreading.

It is contemplated that retaining element 232 can be provisionally fastened to plate 207 with locking fastener 230 threaded partially into hole 229 before placement of plate 207 on the vertebrae. In this manner, retaining element 232 is rotatable with respect to anterior face 212, and can oriented such that holes 208, 209, and 210 are not blocked thereby. After screws 11, 12 and 13 are inserted to secure plate 207 to the vertebrae, retaining element 232 can be oriented to its FIG. 14a position and locking fastener 230 advanced in hole 229 to engage tangs 236.

Referring now to FIGS. 16–19, another embodiment plate 407 is shown. Plate 407 is identical to plates 7, 107 except with respect to the configuration of the retaining elements and their attachment to plate 407, and also in that plate 407 does not include indents for coupling to a plate holder, although the provision of such indents is not precluded. Plate 407 includes edges 416, 417, 418 extending between an anterior face 412 and a posterior face 414. Plate 407 can further include upper protrusion 432 along posterior face 414 for contacting the lower margin of L5. Plate 407 further includes a central hole 436 and a lower instrument engaging hole 438 that can be used to engage an insertion instrument.

Plate 407 includes an upper node 420a, a first lower node 420b and a second lower node 420c each having a screw hole 422a, 422b, 422c, respectively, formed therethrough. Upper retaining element 424a is connected with anterior face 412 of plate 407 by a connecting element 426a that is formed as an integral unit with plate 407 and upper retaining element 424a. A gap 430a is formed between upper retaining element 424a and anterior face 412. Upper retaining element 424a extends at least partially around upper hole 422a and, in its FIG. 16 position, allows entry of a screw 11 through upper hole 422a for attachment to L5. After screw 11 is seated in upper hole 422a, upper retaining element 424a can be bent or deformed from its first form of FIG. 16 to a second form shown in FIG. 19. In its second form upper retaining element 424a extends over upper hole 422a and blocks screw 11 if it were to unseat from upper hole 422a and backout from plate 407.

There is further provided first and second lower retaining elements 424b, 424c associated with first lower node 420b and second lower node 420c, respectively. First and second lower retaining elements 424b, 424c are connected with anterior face 412 of plate 407 by connecting elements 426b, 426c, respectively, that are formed as an integral unit with plate 407 and first and second lower retaining elements 424b, 424c. Gaps 430b, 430c are formed between each first and second lower retaining element 424b, 424c, respectively, and anterior face 412. Each of the first and second lower retaining elements 424b, 424c extends at least partially around a corresponding one of the first and second lower holes 422b, 422c. In their FIG. 16 position, first and second lower retaining elements 424b, 424c allow entry of screws 12, 13 through first and second lower holes 422b, 422c for attachment to S1. After screws 12, 13 are seated in first and second lower holes 422b, 422c, first and second lower retaining elements 424b, 424c are deformed or bent by, for example, applying a bending force, from their first form of FIG. 16 to a second form shown in FIG. 19. In their second form, first and second lower retaining elements 424b, 424c each extend over respective ones of first and second lower holes 422b, 422c and block a corresponding one of the screws 12, 13 if one were to unseat from its hole and backout from plate 407.

Figure 18:
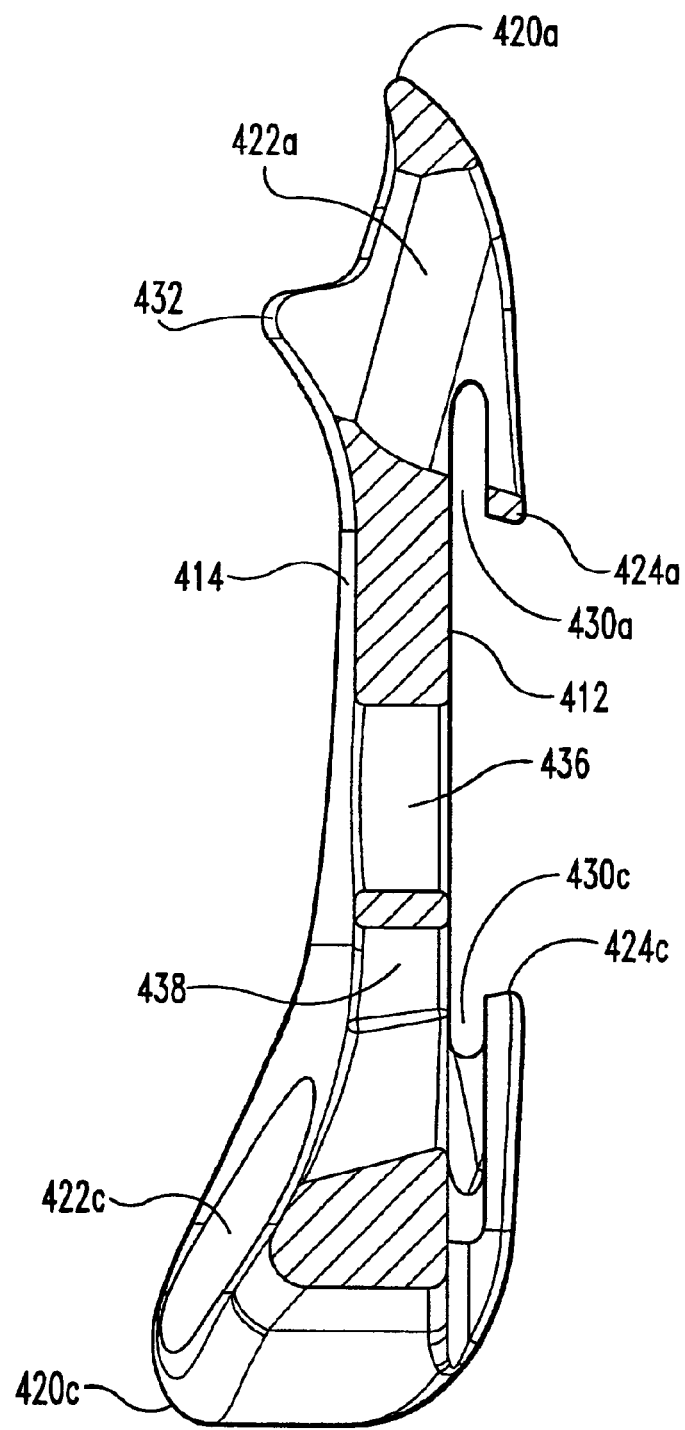
FIG. 18 is a cross-section taken along line 18—18 of FIG. 17.

Plate 407 also provides an alternate arrangement for posterior protrusion 432 intended to contact L5. As shown in FIG. 18, protrusion 432 is intercepted by hole 422a and is thus not continuous along the width of plate 407. In contrast, protrusion 24 of plate 7 is situated below hole 8 and is continuous along the width of prate 7. It should be understood, however, that the location of the L5 posterior protrusion for the plates described herein can be varied based on patient anatomy and either of the above locations for the L5 posterior protrusion can be provided with any of the plate embodiments described herein.

Figure 19:
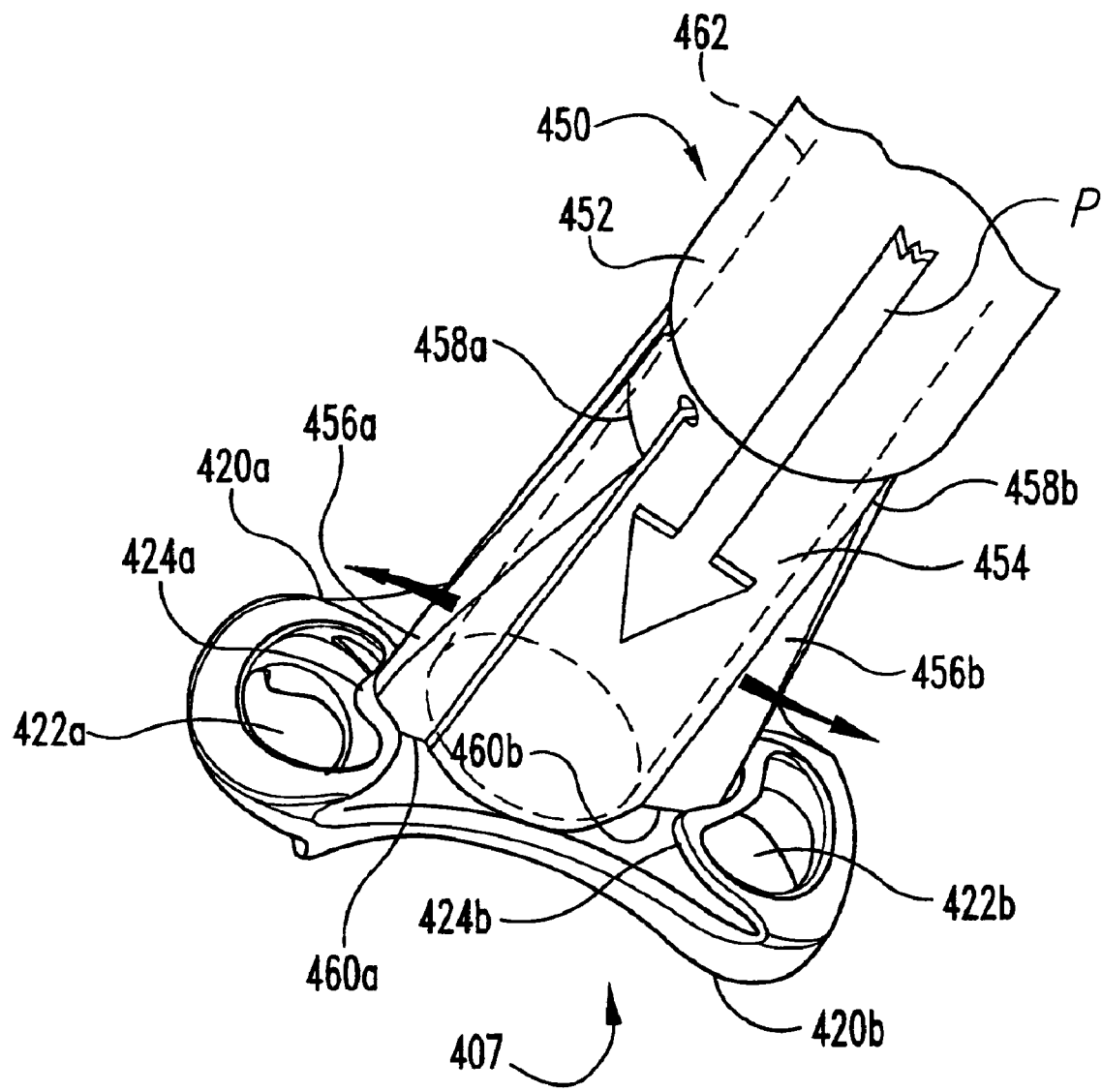
FIG. 19 is a perspective view of a portion of the plate of FIG. 16 with a deformation tool applied thereto.

As also shown in FIG. 19, there is providing a forming tool 450 that is operable to simultaneously apply a bending force to retaining elements 424a, 424b, 424c to move these retaining elements from their first form to their second form overlapping the adjacent plate hole. Tool 450 has an outer shaft 452 coupled to a distal working end 454. Distal working end 454 includes a first forming member 456a positionable adjacent upper retaining element 424a, a second forming member 456b positionable adjacent first lower retaining element 424b, and a third forming member (not shown) positionable adjacent second lower retaining element 424c when tool 450 is mounted on central hole 436 of plate 407. The forming members 456a, 456b are wedge shaped and are pivotally coupled to working end 454 at upper ends 458a, 458b and their opposite thicker lower ends 460a, 460b are normally biased towards the center of shaft 452. An inner actuator 462 housed in outer shaft 452 and working end 454 is movable with respect thereto in the direction of arrow P. Actuator 463 slides distally along the wedge-shaped forming members and pivots their lower ends about their respective upper ends and away from the center of tool 450 into contact with the adjacent retaining element.

Figure 20:
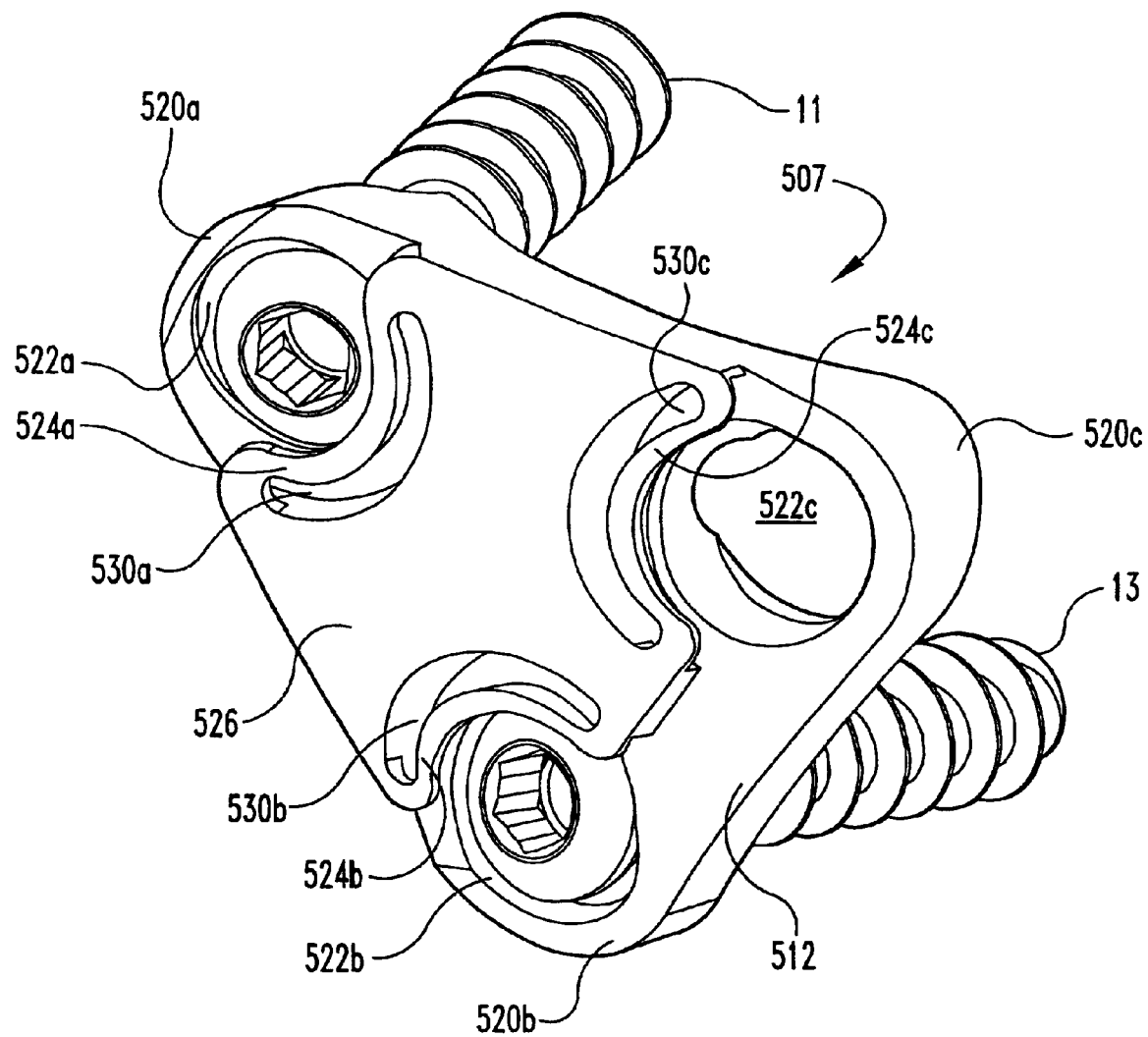
FIG. 20 is a perspective view of another embodiment plate according to the present invention.

Tool 450 is representative of one type of instrument that can be used to bend or adjust the formable retaining elements from their first form to their second form. Other instruments and techniques are also contemplated. For example, the retaining elements can be individually bent or adjusted by a tool inserted into the gap along the retaining element and manipulated therein to apply a bending force. The retaining elements can also be made from a shape memory alloy and temperature applied thereto in order to form the retaining element from their first form to their second form Referring now to FIG. 20, another embodiment plate 507 is shown. Plate 507 is identical to plate 407 except with respect to the configuration of the retaining elements and their attachment to plate 507. Plate 507 includes an upper node 520a, a first lower node 520b and a second lower node 520c each having a screw hole formed therethrough. A base member 526 is connected to or formed as an integral unit with plate 507 and extends from its anterior face 512. Base member 526 has an upper retaining element 524a adjacent upper hole 522a, a first lower retaining element 524b adjacent first lower hole 522b, and a second lower retaining element 524c adjacent second lower hole 522c. Gaps 530a, 530b, and 530c are formed between base member 526 and respective ones of the retaining elements 524a, 524b and 524c. Retaining elements 524a, 524b and 524c are illustrated in FIG. 20 in their first form allowing screw insertion into the adjacent holes. As discussed above with respect to retaining elements of plate 407, retaining elements 524a, 524b and 524c can be bent or otherwise moved into a second form after screw insertion wherein the retaining elements extend over the holes of plate 507 and prevent screw backout.

Figure 21:
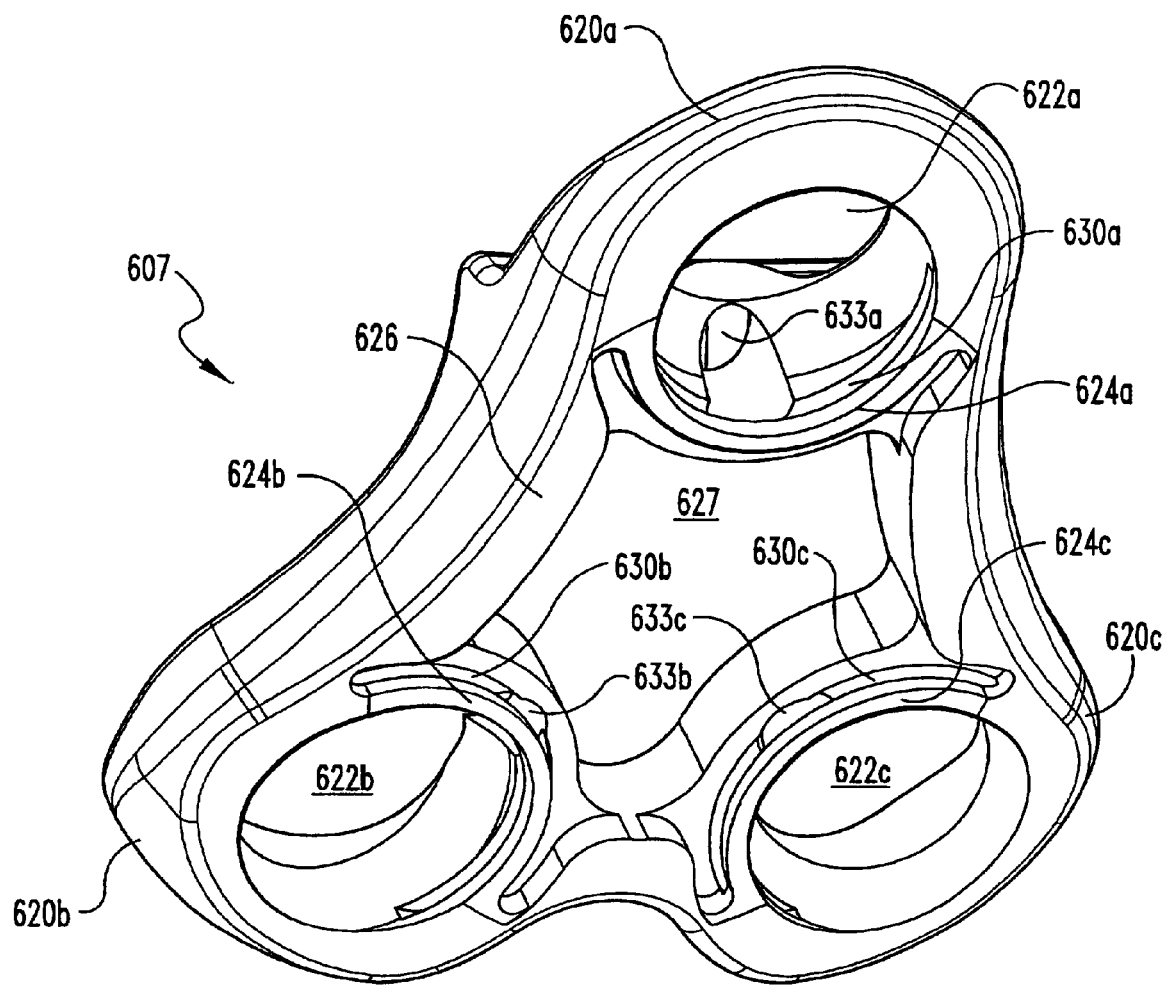
FIG. 21 is a perspective view of yet another embodiment plate according to the present invention.

Referring now to FIG. 21, another embodiment plate 607 is shown. Plate 607 is identical to plate 407 except with respect to the configuration of the retaining elements and their attachment to plate 607. Plate 607 includes an upper node 620a, a first lower node 620b and a second lower node 620c each having a screw hole formed therethrough. Plate 607 includes a wall 626 around its perimeter and around holes 622a, 622b, 622c. Wall 626 forms a central opening 627 in the middle of plate 607, and wall 626 separates central opening 627 and holes 622a, 622b, and 622c. Central opening 627 enables visualization of an implant I in the disc space and accommodates insertion of a forming tool, such as tool 450 discussed above, alongside upper retaining element 624a adjacent upper hole 622a, first lower retaining element 624b adjacent first lower hole 622b, and second lower retaining element 624c adjacent second lower hole 622c.

Gaps 630a, 630b, and 630c are formed between each retaining element 624a, 624b, 624c and wall 626, respectively. Retaining elements 624a, 624b and 624c are illustrated in FIG. 21 in their first form allowing screw insertion into the adjacent holes. As discussed above with respect to retaining elements of plate 407, retaining elements 624a, 624b and 624c can be bent or moved to a second form after screw insertion wherein the retaining elements extend over the holes of plate 607 and prevent screw backout. Further, cutouts 633a, 633b, and 633c are provided in the recess of the hole adjacent retaining elements 624a, 624b, and 624c, respectively, to receive a forming tool inserted therein, which tool can then be pivoted to bend the adjacent retaining element.

Figure 22:
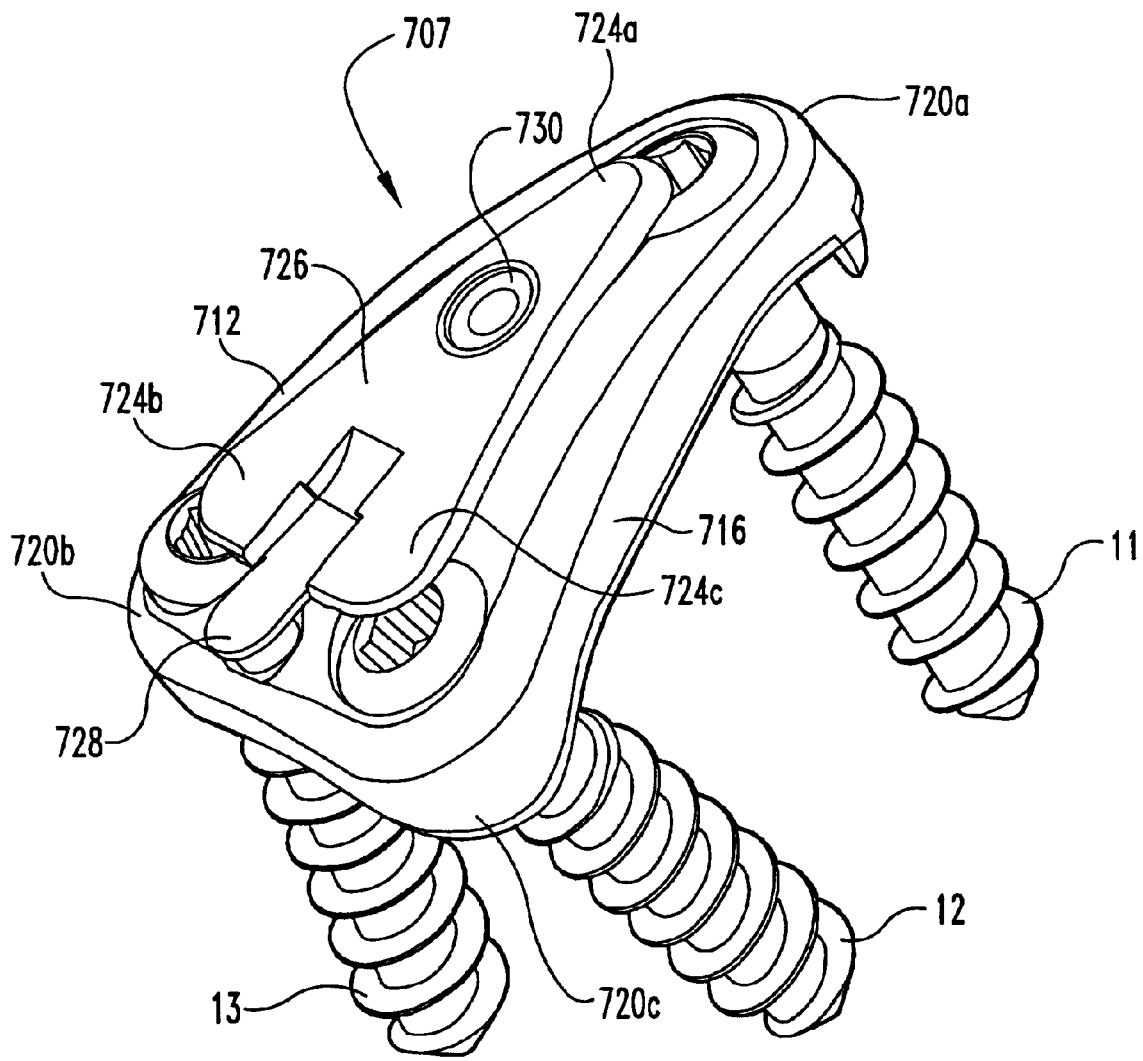
FIG. 22 is a perspective view of still a further embodiment plate according to the present invention.
Figure 23:
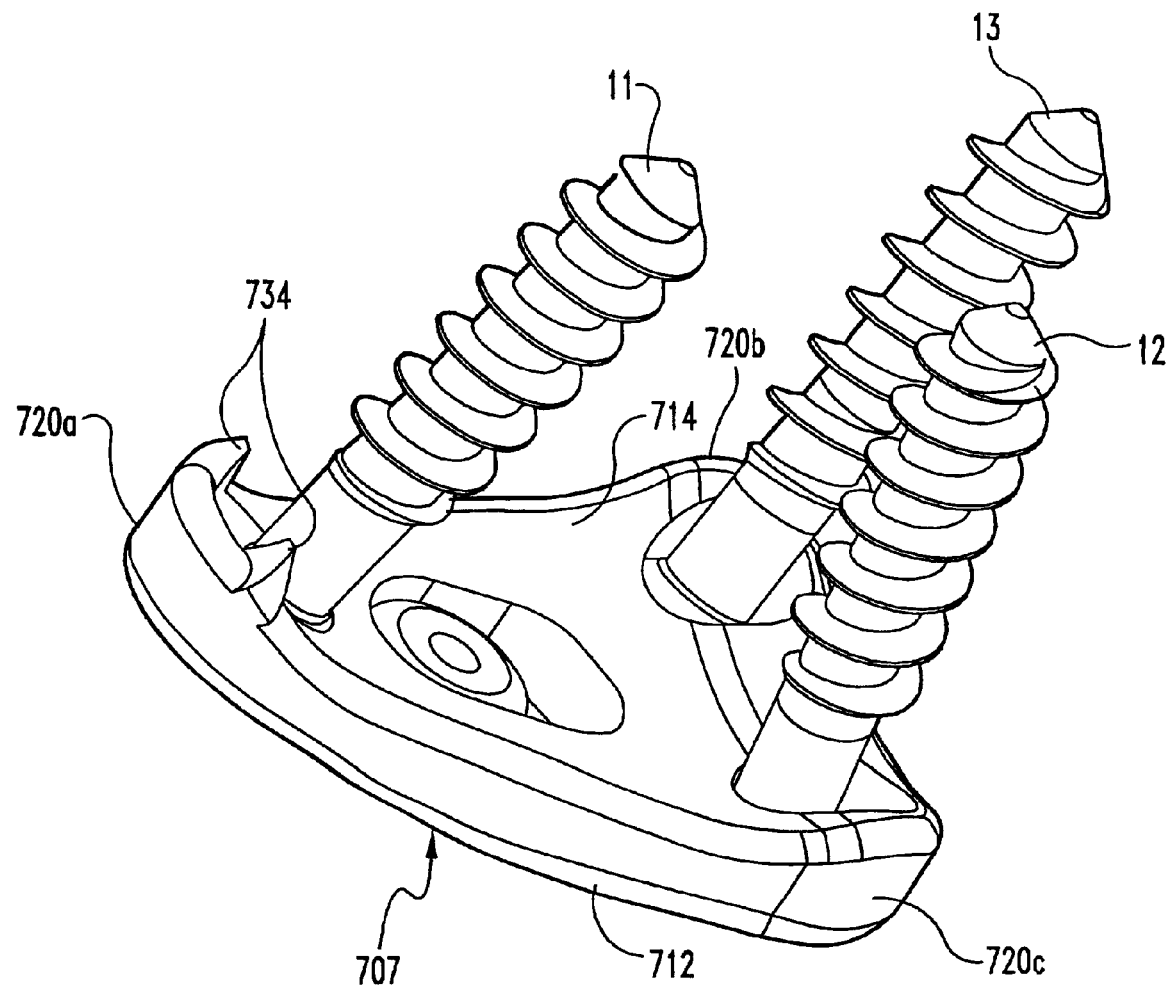
FIG. 23 is a perspective view of the posterior side of the plate of FIG. 22.

Referring now to FIGS. 22–23, another embodiment plate 707 is shown that is (generally the same as the other plate embodiments discussed herein except as otherwise noted below. Plate 707 includes an upper node 720a and first and second lower nodes 720b, 720c. Upper node 720a and lower nodes 720b, 720c each have a hole for receiving a bone screw 11, 12, 13, respectively. Plate 707 further includes an anterior face 712 and an opposite posterior face 714. The edges of plate 707 are not concave between the nodes, but could be provided as such. In this embodiment, plate 707 is provided with a pair of spikes 734 extending from posterior face 714 at the upper end of plate 707. Spikes 714 are embeddable in the upper vertebral body to which the plate is to be secured, such as L5. Such spikes could likewise be provided with any of the plate embodiments described herein.

Plate 707 further includes a retaining element 726 rotatably attached to central hole 736 in the middle of plate 707 by a pin 730. Retaining element 726 has an upper apex 724a, first lower apex 724b and second lower apex 724c. Retaining element 726 has a first position (not shown) wherein retaining element 726 is positioned with respect to plate 707 so that apices 724a, 724b, 724c are not positioned over the screw holes through the plate nodes 720a, 720b, 720c. After screw insertion, retaining element 726 is rotated with respect to plate 707 to position apices 724a, 724b, 724c over the screw holes through nodes 720a, 720b, 720c to prevent screw backout. A spring blade 728 is initially positioned substantially within a slot 732 formed in retaining element 726. Spring blade 728 can be moved out of slot 732 and into contact with anterior face 712 to prevent further rotation of retaining element 726. The orientation between spring blade 728 and anterior face 712 can be such that anterior face 712 biases spring blade 728 upward to provide frictional engagement therebetween causing spring blade 728 to remain in its extended position shown in FIG. 22.

Further embodiments of retaining elements for blocking screws 11, 12, 13 are also contemplated. For example, the anterior face of the plate could be provided with a seat open on one side and bordered by rails or grooves that allow the retaining element to be slidably inserted therein after the screws have inserted. The retaining element could be held in the receiving seat by means of an elastic tongue having formed on its lower face a stud which, upon complete insertion of the retaining element, will penetrate into a receiving seat formed on the anterior surface of the plate Various means are described herein for securing the retaining element on the plate, such as clips, locking fasteners, and pins. Clippable retaining elements, either pre-fitted or not pre-fitted, are advantageous since the retaining element can secured to the plate easily and quickly. The only manipulations by the surgeon required by clippable retaining elements that are not pre-fitted is to move the retaining element in a direction perpendicular to the plate in the space which corresponds to that which was necessary to form anyway for positioning the plate on the spinal column. Use of sliding elements is also contemplated, which necessitate the formation of an additional space to accommodate sliding insertion of the retaining element if not pre-loaded on the plate. The present invention also contemplates retaining elements secured by a threaded fastener and can either be preloaded on the plate or not preloaded on the plate. It should be understood that the present invention contemplates the use of any of the retaining element embodiments described herein with any of the plate embodiments described herein.

Examples of material which may be employed in fabrication of the plates and retaining elements of the present invention can be made from any bio-compatible non-resorbable material, such as titanium, stainless steel, shape memory alloys, and combinations thereof. Resorbable materials are also contemplated. In the embodiments of FIGS. 16–21, the body of the plate can be made from titanium, and the retaining elements made from a shape memory alloy that is formable from the first form allowing screw insertion to the second form for blocking the inserted screws. In another example, the retaining elements can be made from a material less resistant to bending forces than the plate body, which would allow the retaining elements to be more easily bent by the surgeon.

The plate assembly of the present invention may also be used in combination with various types of implants I (FIG. 2). Examples of such implants include interbody spacers, fusion device, and bone graft materials that are placed in disc space D. Further examples of such devices include bone dowels, push-in cages, screw-in cages, tapered cages, cages filled with bone graft and/or graft substitute material or other types of devices suitable for such fusion applications.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A plating apparatus for the spine, comprising:
    a plate having an upper face, a lower face, and at least one hole therethrough extending between said upper and lower faces; and
    a retaining element extending from said upper face adjacent said at least one hole, said retaining element having a first form wherein a screw is insertable into the at least one hole and being formable to a second form wherein at least a portion of said retaining element extends over said at least one hole.

2. The apparatus of claim 1, wherein said retaining element is formed by applying a bending force to said retaining element.

3. The apparatus of claim 1, wherein:
    said plate has a generally triangular shape and includes an upper node and a pair of lower nodes; and
    said at least one hole includes an upper hole through said plate at said upper node to receive a screw for passage into an upper vertebra, a first lower hole in said plate formed through one of said lower nodes to receive a screw for passage into a lower vertebra, and a second lower hole in said plate through the other of said lower nodes to receive a screw for passage into the lower vertebra.

4. The apparatus of claim 3, wherein each of said retaining elements extends from a base member attached to said upper face of said plate.

5. The apparatus of claim 4, wherein there is a gap between said base member and each of said retaining elements.

6. The apparatus of claim 3, wherein said retaining element is positioned adjacent said upper hole and further comprising:
    a first lower retaining element extending from said upper face adjacent said first lower hole; and
    a second lower retaining element extending from said upper face adjacent said second lower hole, wherein said first and second lower retaining elements each have a first form wherein a screw is insertable into the adjacent hole and are formable to a second form wherein at least a portion of said retaining element extends over said adjacent hole.

7. The apparatus of claim 6, wherein each of said retaining elements includes a connecting member integrally formed with said upper face of said plate.

8. The apparatus of claim 7, wherein each of said retaining elements extends around said adjacent hole.

9. A system for securing a plate to a spinal column segment, the system comprising:
    a plate having a generally triangular shape forming three vertices, said plate having a hole adjacent each vertex;
    an instrument including:
        a plate holding portion coupled to said plate and being configured to establish and maintain a defined relative position between said instrument and said plate;
        a shaft having a proximal handle portion and a distal end supporting said plate holding portion; and
        a support extending from said shaft, said support defining three guiding portions, each of said guiding portions corresponding to a respective one of said holes of said plate and arranged to guide a drill to said corresponding hole.

10. The system of claim 9, further comprising a rod coupled to said shaft, said rod terminating in a bearing surface that bears on S1 upon positioning of said plate on the spinal column segment.

11. The system of claim 9, further comprising a pusher that includes means for maintaining a position of said pusher on said plate.

12. The system of claim 9, wherein said plate holding portion is detachable from said shaft.

13. The system of claim 9, wherein the position of said support is adjustable.

14. The system of claim 9, wherein said plate holding portion is attached to a lower edge of the plate.

15. The system of claim 9, wherein said plate holding portion is attached to a hole in the center of said plate.

16. A plating apparatus for the spine, comprising:
    a plate having an upper face, a lower face, and at least one hole therethrough extending between said upper and lower faces; and
    a retaining element extending from said upper face adjacent said at least one hole, said retaining element having a first form wherein a screw is insertable into the at least one hole and being formable to a second form wherein at least a portion of said retaining element extends over said at least one hole, wherein said retaining element is formed by applying a bending force to said retaining element.

17. The apparatus of claim 16, wherein:

said plate has a generally triangular shape and includes an upper node and a pair of lower nodes; and said at least one hole includes an upper hole through said plate at said upper node to receive a screw for passage into an upper vertebra, a first lower hole in said plate formed through one of said lower nodes to receive a screw for passage into a lower vertebra, and a second lower hole in said plate through the other of said lower nodes to receive a screw for passage into the lower vertebra.

18. The apparatus of claim of claim 17, wherein each of said retaining elements extends from a base member attached to said upper face of said plate.

19. The apparatus of claim 18, wherein there is a gap between said base member and each of said retaining elements.

20. The apparatus of claim 17, wherein said retaining element is positioned adjacent said upper hole and further comprising:

a first lower retaining element extending from said upper face adjacent said first lower hole; and a second lower retaining element extending from said upper face adjacent said second lower hole, wherein said first and second lower retaining elements each have a first form wherein a screw is insertable into the adjacent hole and are formable to a second form wherein at least a portion of said retaining element extends over said adjacent hole.

21. The apparatus of claim 20, wherein each of said retaining elements includes a connecting member integrally formed with said upper face of said plate.

22. The apparatus of claim 21, wherein each of said retaining elements extends around said adjacent hole.

23. A plating apparatus for the spine, comprising:

a plate having a generally triangular shape with an upper node positionable along an upper vertebra and a pair of lower nodes positionable along a lower vertebra;

an upper hole in the plate at the upper node to receive a screw for engaging the upper vertebra;

a first lower hole in the plate through one of the lower nodes to receive a screw for engaging the lower vertebra and a second lower hole in the plate through the other of the lower nodes to receive a screw for engaging the lower vertebra; and means for blocking screws inserted in the upper hole and the first and second lower holes, wherein said means for blocking includes a triangular retaining element attached to said plate, said retaining element being movable from a first orientation wherein screws are insertable into each of said upper hole and said first and second lower holes to a second orientation wherein apices of said retaining element extend over respective ones of said upper hole and said first and second lower holes, wherein said retaining element includes a spring blade extendable therefrom to secure said retaining element in said second orientation.

24. The apparatus of claim 23, wherein said retaining element includes a locking fastener extending therethrough and engageable to a central hole in said plate to secure said retaining element in said second orientation.

25. A plating apparatus for the spine, comprising:

a plate having a general triangular shape, said plate having an upper hole near an upper vertex through which a screw is passed for securing said plate to the L5 vertebra, and a pair of lower holes situated near respective ones of first and second lower vertices of said plate, each of said pair of lower holes having a screw passed therethrough to secure said plate to the S1 vertebra; and means for blocking screws seated in said upper hole and said pair of lower holes, wherein said means for blocking screws includes a retaining element threadingly attached to a central hole in said plate, said retaining element being configured to at least partially cover said upper hole and said pair of lower holes.

26. The apparatus of claim 25, wherein said plate includes a posterior face having an edge about said plate, said posterior face including a ridge shaped protrusion adjacent said edge at the upper end of said upper vertex.

27. The apparatus of claim 25, wherein said plate includes a posterior face having an edge about said plate, said posterior face including an anchoring point extending therefrom adjacent said upper vertex.

28. The apparatus of claim 25, wherein said plate includes a posterior face having a generally concave shape.

29. The apparatus of claim 25, wherein said pair of lower holes have an oblong shape extending in the direction toward said upper vertex.

30. The apparatus of claim 25, wherein said retaining element has a substantially circular shape.

31. The apparatus of claim 25, wherein said retaining element has a generally triangular shape.

32. The apparatus of claim 25, wherein said retaining element include three projecting flanges and cutouts between said flanges, whereby each of said flanges is positionable between respective adjacent ones of said upper hole and said pair of lower holes for screw insertion, said retaining element being movable to a second position wherein each of said flanges at least partially covers respective ones of said upper hole and said pair of lower holes.

33. The apparatus of claim 25, wherein said plate includes a posterior face having a protrusion extending along at least part of the width of said plate that bears against a lower lip of an anterior margin of a lower endplate of the L5 vertebra.

34. The apparatus of claim 33, wherein said plate includes on said posterior face adjacent said pair of lower vertices protrusions that bear against a lower margin of an upper endplate of the S1 vertebra.

35. The apparatus of claim 25, wherein said retaining element includes means for fixing said retaining element on said plate either in a first angular position leaving said upper hole and said pair of lower holes completely uncovered, or in a second angular position at least partially covering said upper hole and said pair of lower holes.

36. The apparatus of claim 35, wherein said means for fixing said retaining element includes an elastic tongue including a stud extending from a posterior face of said retaining element, said stud insertable in receiving seats formed on an anterior face of said plate.

37. A plating apparatus for the spine, comprising:

a plate having a general triangular shape, said plate having an upper hole near an upper vertex through which a screw is passed for securing said plate to the L5 vertebra, and a pair of lower holes situated near respective ones of first and second lower vertices of said plate, each of said pair of lower holes having a screw passed therethrough to secure said plate to the S1 vertebra;

a retaining element attachable to a central hole in said plate, said retaining element configured to at least partially cover said upper hole and said pair of lower holes, said retaining element including an elastic tongue with a stud extending from a posterior face of said retaining element, said stud insertable in a receiving seat formed on an anterior face of said plate.

38. The apparatus of claim 37, wherein said plate includes a posterior face having an edge about said plate, said posterior face including a ridge shaped protrusion adjacent said edge at the upper end of said upper vertex.

39. The apparatus of claim 37, wherein said plate includes a posterior face having an edge about said plate, said posterior face including an anchoring point extending therefrom adjacent said upper vertex.

40. The apparatus of claim 37, wherein said plate includes a posterior face having a generally concave shape.

41. The apparatus of claim 37, wherein said pair of lower holes have an oblong shape extending in the direction toward said upper vertex.

42. The apparatus of claim 37, wherein said retaining element has a substantially circular shape.

43. The apparatus of claim 37, wherein said retaining element has a generally triangular shape.

44. The apparatus of claim 37, wherein said retaining element includes three projecting flanges and cutouts between said flanges, whereby each of said flanges is positionable between respective adjacent ones of said upper hole and said pair of lower holes for screw insertion, said retaining element being movable to a second position wherein each of said flanges at least partially covers respective ones of said upper hole and said pair of lower holes.

45. The apparatus of claim 37, wherein said plate includes a posterior face having a protrusion extending along at least part of the width of said plate that bears against a lower lip of an anterior margin of a lower endplate of the L5 vertebra.

46. The apparatus of claim 45, wherein said plate includes on said posterior face adjacent said pair of lower vertices protrusions that bear against a lower margin of an upper endplate of the S1 vertebra.

* * * * *